United States Patent
Morales et al.

(10) Patent No.: US 6,551,102 B1
(45) Date of Patent: Apr. 22, 2003

(54) DENTAL ARTICULATOR APPARATUS INCLUDING MOLDS INCORPORATING POSITIONING AND RETENTION MEANS FOR UPPER AND LOWER DENTAL CASTS AND PORTIONS THEREOF

(75) Inventors: David H. Morales, El Sobrante, CA (US); Marek J. Jez, Campbell, CA (US)

(73) Assignee: Artic-A-Jig, LLC, Pinole, CA (US)

( * ) Notice: Subject to any disclaimer, the term of this patent is extended or adjusted under 35 U.S.C. 154(b) by 0 days.

(21) Appl. No.: 08/887,478

(22) Filed: Jul. 2, 1997

(51) Int. Cl.$^7$ ................................................ A61C 11/00
(52) U.S. Cl. .......................................... 433/60; 433/54
(58) Field of Search ................................. 433/54, 57, 58, 433/60–67

(56) References Cited

U.S. PATENT DOCUMENTS

| | | | | | |
|---|---|---|---|---|---|
| 565,326 | A | * | 8/1896 | Bragg | 433/64 |
| 1,343,691 | A | * | 6/1920 | Stanbrough | 433/66 |
| 1,684,393 | A | * | 9/1928 | Gysi | 433/67 |
| 1,989,367 | A | * | 1/1935 | Keeney | 433/58 |
| 3,078,577 | A | * | 2/1963 | Prentki | 433/66 |
| 4,189,837 | A | * | 2/1980 | Stele | 433/67 |
| 4,200,981 | A | * | 5/1980 | Fine | 433/60 |
| 4,299,570 | A | * | 11/1981 | Yogosawa | 433/65 |
| 4,412,822 | A | * | 11/1983 | Blechner | 435/57 |
| 4,439,151 | A | * | 3/1984 | Whelian | 433/60 |
| 4,538,987 | A | * | 9/1985 | Weissman | 433/60 |
| 4,608,016 | A | * | 8/1986 | Zeiser | 433/60 |
| 5,425,636 | A | * | 6/1995 | Ghim | 433/64 |

* cited by examiner

Primary Examiner—Ralph A. Lewis
(74) Attorney, Agent, or Firm—John J. Leavitt

(57) ABSTRACT

Dental articulator apparatus includes a base articulator plate and a top articulator plate mounted on a support stanchion. On confronting surfaces of the top and base articulator plates are formed confronting mold cavities that receive dental "stone" mixed to a "workable" consistency so that the cavities can be filled with plastic "stone" to reconstruct from a "negative" impression a "positive" replica of a patient's teeth in stone. A press ejects the dental stone casting from the mold cavity in which it is formed. Embedded in the stone casting is a plastic sleeve. The plastic sleeve slidably accommodates a guide pin that passes through the cavity wall. To remove the dental stone casting from the mold cavity, the guide pin is first removed by sliding it out of the plastic sleeve. The ejected dental casting may be segmented to separate one stone "tooth" from another. A portion of the embedded tubular sleeve remains in each of the stone "tooth" segments. The separated dental casting segment of each of the teeth, or group of teeth, when reinserted into the mold cavity in its original position, is secured in that position by reinstating the guide pin. Both the base and top articulator plates may be pivotally and slidably mounted on the support stanchion for universal accommodation of upper "teeth" with lower "teeth" in the same manner in which the mandibular joints in the human jaw function to accommodate upper and lower teeth in humans.

19 Claims, 9 Drawing Sheets

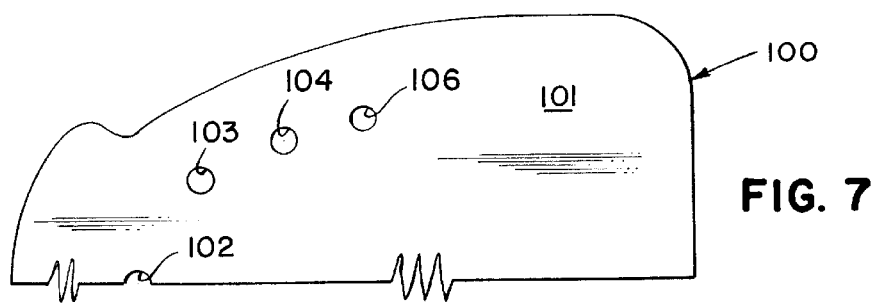
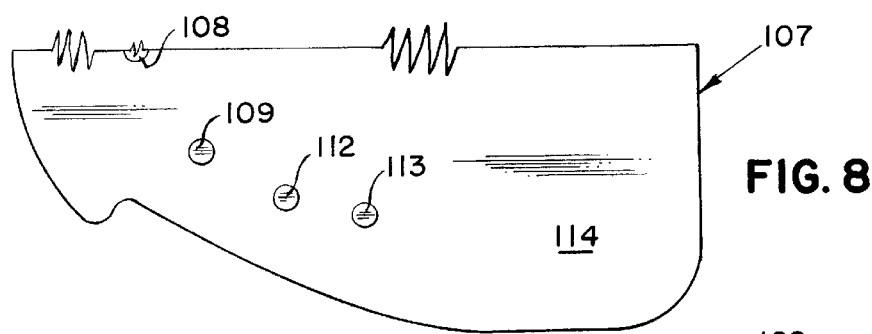
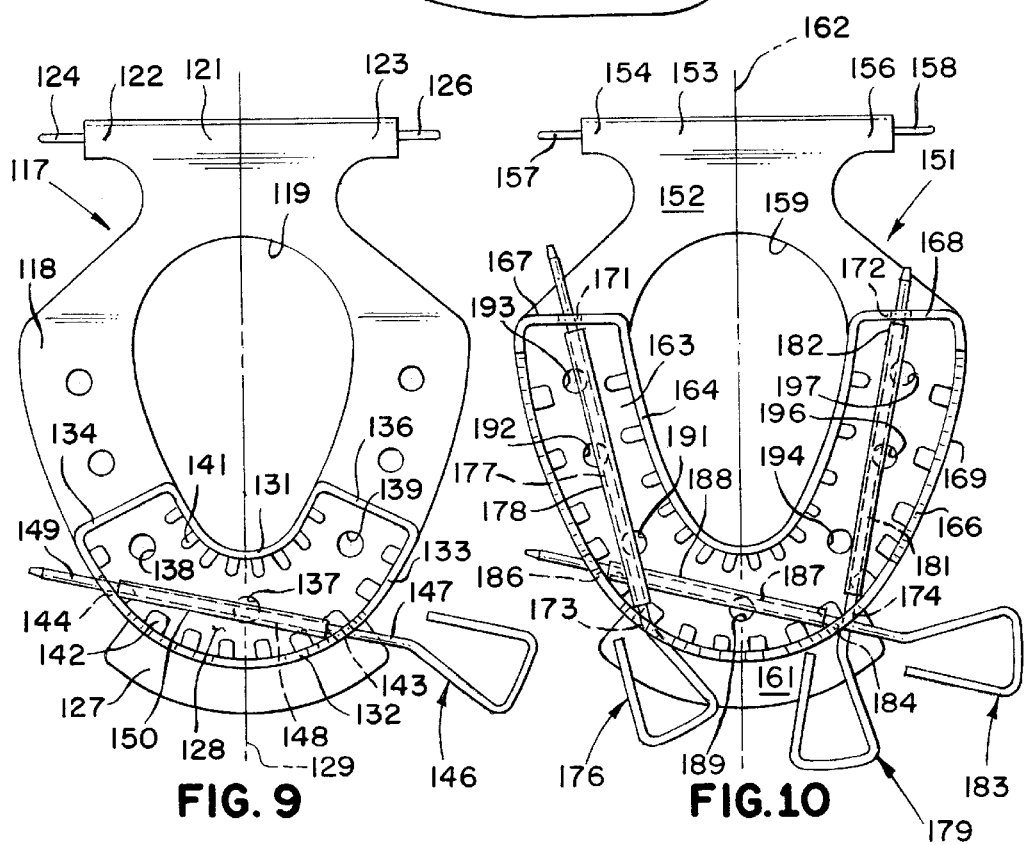

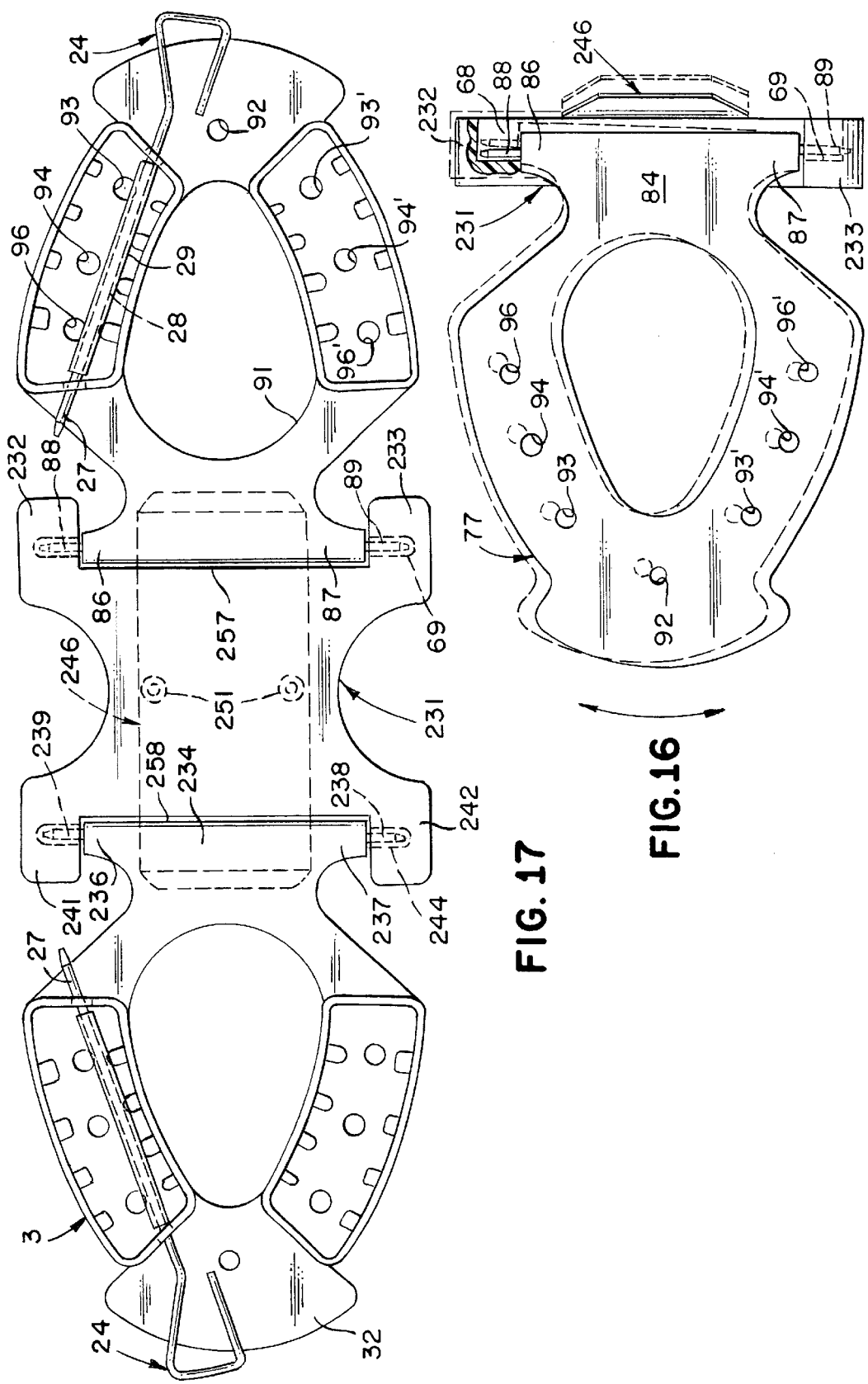

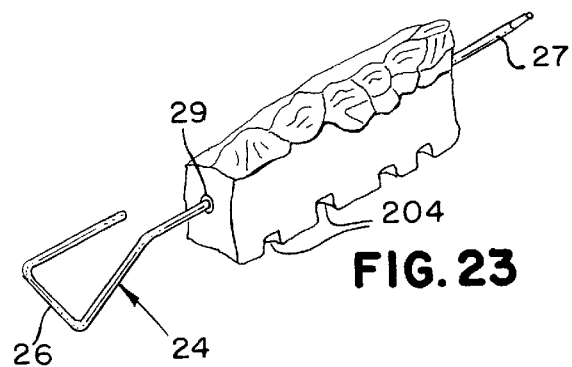
FIG. 23
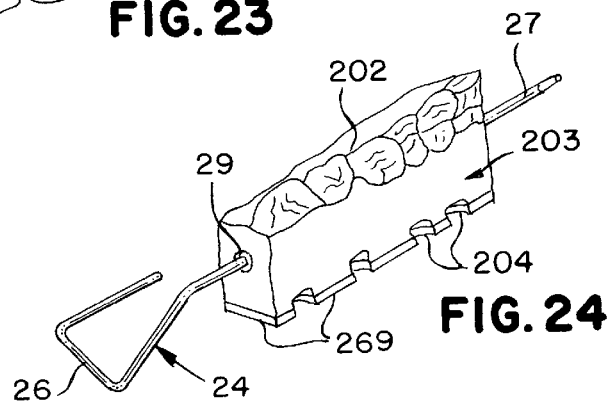
FIG. 24
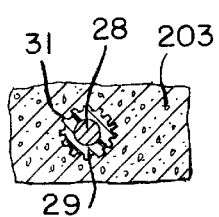
FIG. 27
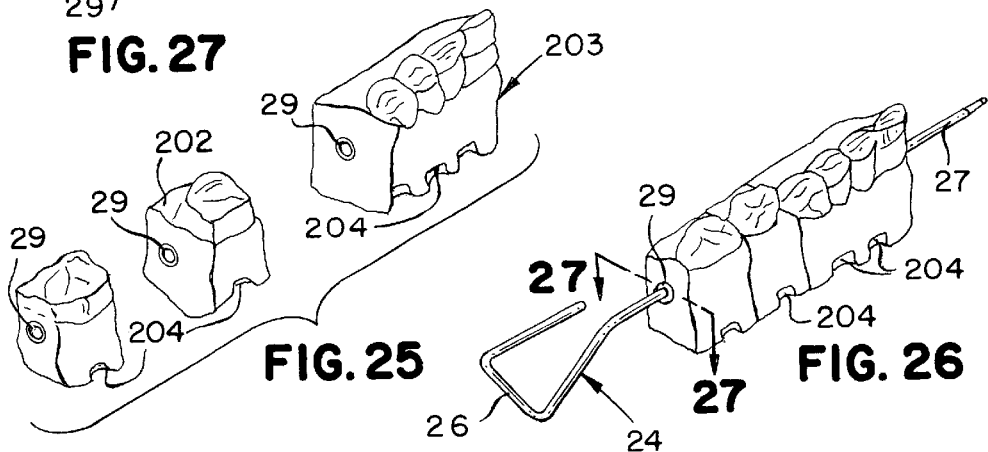
FIG. 25
FIG. 26
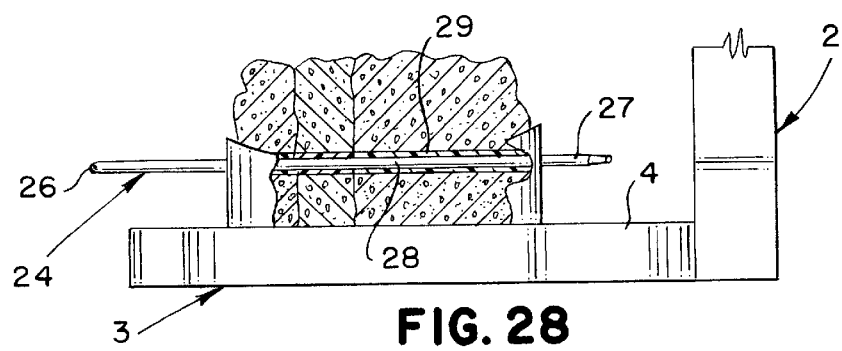
FIG. 28

DENTAL ARTICULATOR APPARATUS INCLUDING MOLDS INCORPORATING POSITIONING AND RETENTION MEANS FOR UPPER AND LOWER DENTAL CASTS AND PORTIONS THEREOF

BACKGROUND OF THE INVENTION

1. Field of the Invention

This invention relates to dental articulator apparatus, and particularly to upper and lower dental mold forms within which upper and lower tooth forms, or portions thereof, may be cast, removed from the mold forms, segmented as necessary, and the segments accurately repositioned and retained in the mold form.

2. Description of the Prior Art

A preliminary patentability and novelty search has revealed the existence of the following patents:

| | | |
|---|---|---|
| 4,412,822 | 4,449,929 | 4,451,234 |
| 4,460,338 | 4,496,320 | 4,533,323 |
| 4,548,581 | 4,611,991 | 4,696,319 |
| 4,721,463 | 4,734,003 | 4,744,751 |
| 4,786,253 | 4,797,097 | 4,946,388 |
| 5,006,065 | 5,007,829 | 5,020,993 |
| | 5,044,949 | |

All of the above listed patents relate to the subject matter of fabricating dental devices by one method or another, and utilize an articulator device of one design or another. However, as will readily be apparent from a detailed examination of the patents listed above, they involve complex procedures and complex equipment that requires a great deal of training and skill to operate to fabricate artificial dental devices having the precise size and configuration that is required by the dental profession. Specifically, the process taught by the patents listed above involve the use of too much labor and the use of too much "stone", which is the material that is utilized to replicate a patient's mouth and teeth from the impression that is delivered to the dental laboratory by a dentist.

It will of course be understood that when a dentist utilizes a hardenable plastic material to make an impression of a patient's teeth, the mass of hardenable plastic material is permitted to harden in the patient's mouth until the exact configuration of the teeth and gum structure of the patient is impressed in the material, thus creating a "negative" of the patient's dental pattern, be it the entire number of upper and lower teeth, or only a portion of either or both of the upper and lower teeth. These impressions that are made by the dentist and supplied to the dental laboratory replicate with considerable exactitude and precision the configuration of the patient's teeth and particularly the occlusive surfaces thereof which of course must match exactly in opposing teeth in the upper and lower jaws.

The impression thus made by the dentist is then sent to the dental laboratory and under conventional circumstances, the impression would be utilized to reproduce in a hardenable material such as "stone" commonly used by dental laboratory technicians the exact pattern and configuration that is represented by the "negative" impressions taken from the patient's mouth. By conventional methods and conventional articulators as illustrated in the patent listed above, the reproduction of the patient's crown pattern is a labor intensive process, thus increasing the cost of the work to both the dentist and to the patient. Accordingly, it is one of the objects of the present invention to simplify the process of reproducing the exact configuration and pattern of the patient's teeth through utilization of a novel dental articulator that is less costly to produce and requires less skill to utilize to produce dental casts of a patient's teeth.

Another object of the invention is the provision of a dental articulator apparatus or kit that utilizes selectively, dental casting molds for specific portions of a patient's dental array.

A still further object of the invention is the provision of a dental articulator apparatus and kit in which a mold is utilized in which the dental pattern of a patient is cast in dental stone, which cast can then be removed from the mold after hardening, individual teeth in the casting can then be separated one from the other and then reinserted into the mold and retained in exactly the same position in which they were initially cast so that any one or a number of the multiple teeth initially cast may be individually or as a group removed from the casting mold to enable the dental technician to complete the operation of forming an individual or a multiple denture structure for the patient that will fit precisely in the patient's mouth without the necessity of laborious and time consuming and expensive trimming in order to make the artificial dental device fit the patient's mouth.

A still further object of the invention is the provision of a dental casting mold that incorporates peripheral locating lugs in the base of the mold that creates recesses of complementary configuration and location in the dental casting cast in the mold, so that when the dental casting is removed from the mold, it may be replaced in exactly the same position in which it was originally cast because the recesses made in the casting correspond to the locating lugs or "fillets" formed in the mold.

A still further object of the invention is the provision of a method and means of permanently embedding one or more guide tubes in the dental casting through which a removable metal guide pin may be inserted and supported on the mold prior to pouring the dental pattern, and which forms an elongated sleeve embedded in the casting and enables the dental pattern and the sleeve to be cut into multiple independent tooth segments and reinserted into the mold as individual teeth and retained in exactly the same position in which such casting was initially produced by reinsertion of the metal pin through the now segmented sleeve and body of the casting.

Yet another object of the invention is the provision of two alternate embodiments of the dental articulator apparatus of the invention, the differences between the two embodiments involving simplification of structure and facility of use.

A still further object of the invention is the provision of a dental articulator apparatus in which opposing dental casting mold plates are automatically and simultaneously resiliently centered in relation to a supporting stanchion so as to provide exact correspondence between upper and lower tooth castings.

Another object of the invention is the provision of a dental articulator apparatus incorporating a mold plate retention stanchion, and means resiliently and releasably retaining the mold plates on the retention stanchion, and enabling pivotal displacement of the mold plates in relation to the retention stanchion to change their orientation in relation thereto while retaining the mold plates releasably secured to the retention stanchion.

A still further object of the invention is the provision of a press structure that cooperates with the dental articulator tray or mold to eject the stone dental casting from the mold after the casting has hardened.

The invention possesses other objects and features of advantage, some of which, with the foregoing, will be apparent from the following description and the drawings. It is to be understood however that the invention is not limited to the embodiment illustrated and described, since it may be embodied in various forms within the scope of the appended claims.

SUMMARY OF THE INVENTION

In terms of broad inclusion, the dental articulator apparatus of the invention in one preferred embodiment includes a base plate fixedly secured by one end to a monolithic stanchion or main support bar or plate that normally extends from the base plate perpendicularly and which at its top end pivotally supports a top plate that may be articulated from a horizontal position to a vertical position, and which is detachably secured to the upper end of the stanchion or support plate. On confronting surfaces of the top plate and base plate, are formed mold cavities the walls of which project perpendicularly from the confronting surfaces of the top and base plates, so that the mold cavities confront one another, in much the same manner that the upper and lower set of teeth in a patient's mouth confront one another when the mouth is closed. The mold cavities formed in the base and top plate are utilized to receive dental "stone" that has been mixed to a consistency to be "workable" yet not be liquidous or runny, so that each of the cavities can be independently filled with the still plastic "stone" and the "negative" impression received from the dentist superimposed over the stone filled cavity so as to reconstruct the "positive" impression of the patient's teeth in stone when it sets up and hardens. It is important to note that the dental "stone" should be vibrated in the mold cavity so as to remove air bubbles that may be entrained in the mixture when the "stone" in powdered form is mixed with water to render it "plastic" or "workable". Once the dental stone casting has hardened, means are provided for ejecting the dental stone casting from the mold cavity in which it is formed. Embedded in the hardened dental stone casting is an elongated tubular sleeve, preferably fabricated from a suitable plastic material. The outer diameter of the tubular sleeve is conveniently approximately ⅛ of an inch or less, and the hollow interior of the plastic tube snubly yet slidably accommodates a metal guide pin that passes through two appropriate apertures formed in the mold wall while the ends of the plastic tube abut the inner surface of the mold cavity. When the dental stone casting has hardened, and it is desired to remove the dental stone casting from the mold cavity, the guide pin is removed by sliding it out of the plastic sleeve, which remains embedded in the stone casting. The mold plate is appropriately mounted in a press that is manipulated to eject the "positive" dental casting from the mold as one monolithic body. The plastic tubular sleeve remains embedded in the monolithic body when it is ejected from the mold cavity. Thereafter, the monolithic dental casting may be segmented so as to separate one stone "tooth" from another. The process of separation is conveniently effected with an appropriate stone cutting electrically driven saw or a fine tooth hand saw. The segmenting process severs the embedded tubular sleeve so that a portion thereof remains in each of the stone tooth segments that have been separated from the remainder of the casting. Additionally, orienting lugs are formed in the lower peripheral portion of the mold cavities so that the dental castings, when separated, may be reinstated into the casting cavity in exactly the same position in which they were originally cast by virtue of orienting lugs fitting snugly in complementary recesses formed in the stone casting. Additionally, because the tubing imbedded in each of the now separated dental casting segments remains embedded, the separated dental casting segment of each of the teeth, or group of teeth, when reinstated into the mold cavity in its identical original position in which it was originally cast, may be secured in that position by reinserting the guide pin through the aligned tubular sleeve segments embedded in the separated tooth castings. Preferably, a full set of mold cavities includes a mold cavity for the front teeth comprising the central incisors, lateral incisors, and canine teeth, while another set of cavity molds includes the left and right side molars extending from the first pre-molar to at least the second molar and perhaps even the third molar which constitutes the wisdom tooth. The third set of mold cavities is designed to encompass all of the upper and lower teeth in a patient's mouth. In another preferred embodiment, both the base plate and top plate are pivotally and slidably mounted on the retaining stanchion for universal accommodation of upper "teeth" with lower "teeth" in the same manner in which the mandibular joints in the human jaw function to accommodate upper and lower teeth in humans.

BRIEF DESCRIPTION OF THE DRAWINGS

FIG. 7 is a fragmentary top plan view of one-half of the spacer plate illustrated in FIG. 2, illustrating the position of the pin-receiving apertures in the spacer plate. The view is taken in the direction of the arrows shown on the line 7—7 in FIG. 2.

FIG. 8 is a fragmentary top plan view of one-half of the ejector plate illustrated in FIG. 3 taken in the plane indicated by the line 8—8 in FIG. 3, and showing the location of the ejector pins secured to the ejector plate and which are adapted to penetrate the pin-receiving apertures as shown in FIG. 11.

FIG. 9 is a top plan view of a maxillary dental casting plate appropriate for the upper front teeth of a patient's mouth, shown apart from the articulate frame illustrated in FIG. 1, and indicating the guide pin and resilient tubular sleeve.

FIG. 10 is a view similar to FIG. 9 but illustrating a mold cavity plate suitable for use for replicating the configuration, placement and occlusive surfaces of all of the maxillary and mandibular teeth of a patient's mouth. Guide pins are shown extending through a mold cavity and surrounded within the mold cavity by plastic tubing.

FIG. 16 is a top plan view of the maxillary cavity plate taken in the plane indicated by line 16—16 in FIG. 14, a portion of the stanchion broken away to illustrate the pivotal, slidable and resilient mounting of the upper maxillary plate.

FIG. 17 is a top plan view of the second preferred embodiment of the dental articulator apparatus with the maxillary and mandibular mold cavity plates shown pivoted away from one another and retained in extended form in essentially a common plane with the support stanchion.

FIG. 23 is a perspective view of the hardened "positive" tooth casting produced through use of the first embodiment of FIGS. 1–13, and shown apart from the mold plate and with the guide rod reinserted through the tubular sleeve embedded in the casting.

FIG. 24 is a view similar to FIG. 23, but illustrating the hardened "positive" tooth casting produced through use of the second embodiment of FIGS. 14—22, and shown apart from the mold plate and with the guide rod reinserted through the tubular sleeve embedded in the casting, and showing the aperture seal floor plate attached to the underside of the casting.

FIG. 25 is a perspective view illustrating the dental casting after the guide pin has been removed leaving behind the plastic sleeve, then removed from the mold cavity and segmented into three separate pieces, each including a segment of the plastic tubing embedded therein.

FIG. 26 is a perspective view illustrating how the three separate segments illustrated in FIG. 25 may be reassembled by re-inserting the guide pin through the segmented and embedded plastic tube segments.

FIG. 27 is an enlarged cross-sectional view illustrating the plastic tube embedded in the casting material.

FIG. 28 is a fragmentary elevational view of the base casting plate showing the dental casting reassembled and re-inserted in the casting activity with the guide pin reinserted to retain the now separated dental segments in the original position in which they were cast.

DESCRIPTION OF THE PREFERRED EMBODIMENTS

In the interest of brevity in this description, a first preferred embodiment as illustrated in FIGS. 1–13 will be explained in detail. Thereafter the differences in structure, function and mode of operation of a second embodiment in comparison with the first embodiment will be explained.

Thus, in terms of greater detail, the dental articulator apparatus of the invention in both embodiments comprises a multiplicity of cooperating components used together, and individually at different times, and all functioning for the purpose of emulating the movement of the lower mandible jaw and the teeth fastened therein in relation to the upper maxillary teeth in the mouth of the patient. Basically, one purpose of the invention is to enable a dental laboratory to expeditiously, and relatively inexpensively when compared to conventional articulator devices, reconstruct a tooth or teeth structures of a patient upon request by a dentist. Two of these functions performed by dental laboratories includes the fabrication of crowns to be imposed on and secured to a tooth stump that has been formed to receive it, and the fabrication of an artificial tooth or teeth to fill the gap left by the removal of one or more teeth between existing and secure teeth. It is to facilitate these functions that the dental articulator apparatus of this invention excels when compared with the labor intensive procedures required by prior art dental articulators as represented by the prior art patents listed above. However, another advantage of the dental articulator apparatus of this invention is the saving that occurs from diminishing the amount of materials that are required to cast a replica of the patient's teeth, taken alone or as a group less than the total number of teeth in the patient's mouth, or including all of the teeth in the patient's mouth.

Figure 1:
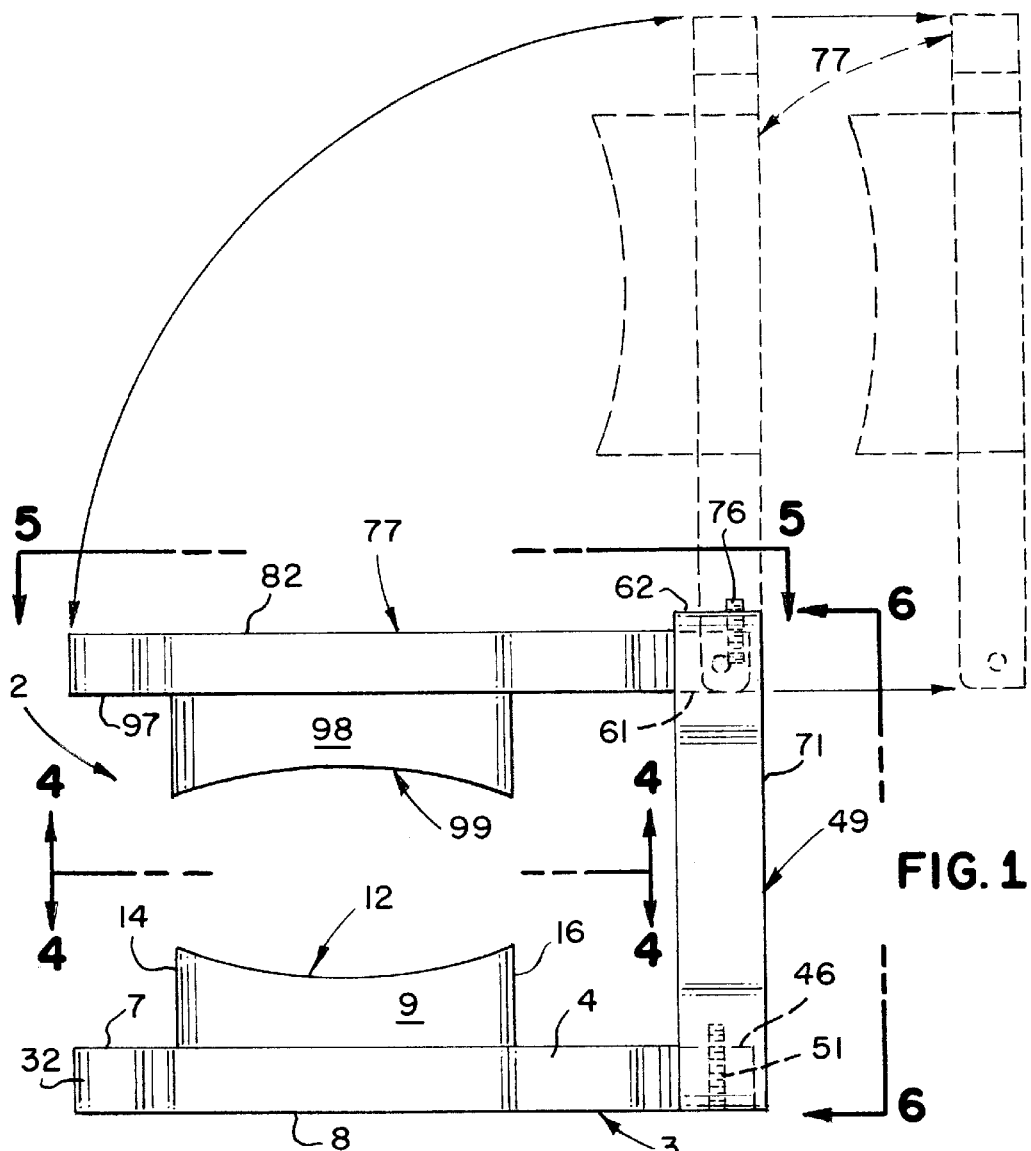
FIG. 1 is a side elevational view of one preferred embodiment of the articulator apparatus including one set of upper and lower mold cavities that are appropriate for casting confronting quadrant plates. Articulation of the top plate is indicated in broken lines, as is the detachability of the top plate from the supporting stanchion.

Referring to the drawings, particularly FIGS. 1–13 as they relate to a first embodiment of the invention, and specifically to FIG. 1, it will there be seen that the dental articulator apparatus is illustrated and designated generally by the numeral 2. The apparatus includes in this first embodiment a base or mandibular member designated generally by the numeral 3. The base member is preferably fabricated from a tough synthetic resinous material of the type sold under the trademark Delrin. The base member 3 includes a base plate 4 conveniently having a thickness of approximately ⅜ of an inch, and configured symmetrically with respect to a central longitudinal axis 6. The base plate is provided with a top surface 7 and a bottom surface 8. Referring to FIG. 4, on the top surface 7 of the base plate 4, there is integrally formed and perpendicularly extending peripheral walls designated generally by the numeral 9 of a mold cavity 12, the bottom of which cavity is formed by an enclosed portion of the top surface 7. The peripheral walls include an inner peripheral wall 13, having a concave upper edge, a forward wall 14, an outer wall 15 also provided with a concave upper edge an a rear wall 16. Interiorly of the cavity, and formed in the juncture between the bases of inner and outer peripheral walls 13 and 15 and top surface 7 of the base plate within the cavity 12, are a multiplicity of randomly spaced lugs or fillets 17 which merge smoothly with the inner surface 18 of the peripheral walls 13 and 15. Preferably, the lateral width of each of the fillets varies from one to the other, no two of the fillets being the same width. The fillets produce recesses in the dental stone casting that enable the entire casting, or portions thereof, to be reassembled in the cavity in exactly the same position after having been ejected from the cavity.

In like manner, referring to the inner peripheral wall portion 13, it will be seen that a multiplicity of randomly spaced fillets 19 are provided, these fillets also being of random width, no two of the four illustrated being of the same width. Like fillets 17, the fillets 19 merge smoothly with the inner surface 21 of the inner peripheral wall 13, while the lower edges of the fillets 17 and 19 are intercepted by the top surface 7 of the plate 4. As seen in FIG. 4, the mold cavity 12 lies on one side of the central axis 6, and there is provided on the opposite side of the central axis 6, a complementary cavity 12' incorporating the same elements previously discussed with respect to the cavity 12, and identified by identical primed reference numbers.

With respect to the cavities 12 and 12', it will be seen that the forward walls 14 and 14' are provided with apertures 22, and the rear walls 16 and 16' are provided with an apertures 23. Extending through the apertures 22 and 23 of cavity 12', as shown in FIG. 4, is an elongated guide pin designated generally by the numeral 24 and including a proximal end 26 that forms a digitally manipulate handle, and a distal end 27 that is sharpened as illustrated to facilitate passage of the intermediate shank portion 28 of the guide pin through a tubular plastic sleeve 29 that is interposed between the end walls 14' and 16' and retained in this position by the intermediate portion 28 of the guide pin. The guide pin 24 is preferably fabricated from stainless steel, and the surrounding tubular member 29 is fabricated from a synthetic resinous material to have an outer diameter of approximately ⅛ of an inch, and an inner diameter sufficient to snugly and slidably receive passage therethrough of the guide pin 24. Preferably, as illustrated in FIG. 27, the outer periphery 31 of the synthetic resinous sleeve or tube 29 is knurled as shown to provide radially outwardly extending projections which function to lock the tubular sleeve in position when it is embedded in dental stone as will hereinafter be explained. Obviously a guide pin could also be inserted through apertures 22 and 23 in cavity 12, but is omitted here in the interest of clarity.

Referring again to FIGS. 1 and 4, it will be seen that the base plate 4 projects forwardly of the cavities 12 and 12' and cavity walls 14 and 14', respectively, in an arcuate portion 32 defined by a forward peripheral arcuate surface 33 and the inner arcuate peripheral surface 34 formed by a generally egg-shaped aperture 36 formed in the base plate 4. It should be noted from FIG. 4 that the inner arcuate peripheral surface 34 of the aperture coincides with the outer surfaces of the inner peripheral walls 13 and 13', thus establishing the relationship of the cavities 12 and 12' as being substantially convergent from the rear walls 16 and 16' toward the front walls 14 and 14' and the associated base plate portion 32 that projects beyond the limits of the front walls of the cavities. The purpose of this convergent relationship is to generally position the cavities in the general relationship of human teeth. Formed in the forwardly projecting base portion 32 is an aperture 37 formed symmetrically on the axis 6, and corresponding in diameter to apertures 38, 39 and 41 formed within the base plate 4 within the cavity 12. Similar apertures 42, 43, and 44 are formed in the base plate 4 within the cavity 12' as illustrated. The purpose of these apertures is to facilitate ejection of the hardened dental stone casting from the cavity.

Figure 6:
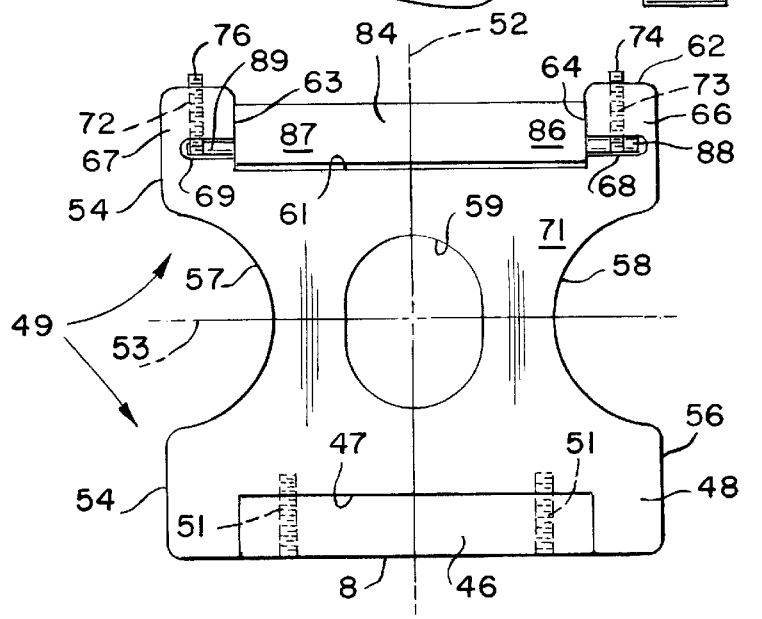
FIG. 6 is an end elevational view of the support stanchion taken in the direction of the arrows on line 6—6 in FIG. 1.

The base plate 4 is also provided with an end mounting portion 46 shown broken away in FIG. 4, but shown in broken lines in FIG. 1 and full lines in FIG. 6. The mounting portion 46 of the base plate 4 extends into a generally rectangular slot 47 formed in the base portion 48 of a monolithic stanchion member designated generally by the numeral 49. The mounting portion 46 of the base plate 4 in this preferred embodiment is rigidly secured within the slot 47 by appropriate screws 51. Thus, the base member 3 in this embodiment is securely yet detachably fastened immovably in relation to the stanchion 49.

Referring to FIGS. 1 and 6, it will be seen that the stanchion 49 is generally quadrilateral in configuration, having a thickness of approximately ½, and preferably being fabricated from the same synthetic resinous material from which the base member 3 is fabricated, namely, a synthetic resinous material sold under the trademark Delrin. Obviously, equivalent or other materials that provide a hard and rigid non-brittle member may also be used. As illustrated in FIG. 6, the stanchion 49 is constructed substantially symmetrical with respect to a vertical axis 52 and a horizontal axis 53.

Centrally of the axis 53, the side edges 54 and 56 are provided with semi-circular recesses 57 and 58, respectively, while a generally ovate aperture 59 is formed symmetrically about the intersection of the axes 52 and 53 as shown. The recesses 57 and 58, and the aperture 59 reduce the amount of synthetic resinous material needed to form the stanchion member, thus reducing the cost, and function further as means by which the stanchion with the assembly of mold cavity plates may be digitally manipulated, i.e., the recesses 57 and 58 and the aperture 59 provide locations where the fingers of one hand may grasp the stanchion so as to manipulate it during use as will hereinafter be explained.

Also formed in the stanchion 49, symmetrical with respect to the vertical axis 52, is a slot 61 as seen in FIGS. 1 and 6, the bottom of the slot 61 being spaced downwardly from the top edge 62 of the stanchion, while the end surfaces 63 and 64 of the slot are formed parallel, respectively, to the outer edges 54 and 56, and spaced inwardly therefrom to provide parallel mounting portions 66 and 67 spaced equally on opposite sides of the vertical axis 52. Formed in a laterally extending direction in the left and right wall surfaces 63 and 64 of the slot 61 formed between mounting portions 66 and 67 are laterally extending slots 68 and 69 that have a depth measured from the rear surface 71 of the stanchion to about the mid-point thereof as seen in FIG. 1.

Additionally, formed in each of the mounting portions 66 and 67 through the top edge surface 62 of each are threaded bores 72 and 73 that communicate with the transversely extending slots 68 and 69. The bores 72 and 73 receive set screws 74 and 76 that may selectively be threadably advanced into the mounting portions 66 and 67 sufficiently to intercept the transverse slots 68 and 69. From FIG. 1, it will be seen that the bores 72 and 73 are positioned laterally closer to the rear surface 71, or stated in other words, intermediate the open ends of the slots and the closed ends thereof. It should of course be understood that while the lower cavity plate 3 has been described and illustrated as being rigidly secured by screws 51, alternatively the lower cavity plate may be mounted to the stanchion in the same manner as the top plate, which is hereinafter described in relation to the embodiment illustrated in FIGS. 14–17.

Pivotally and slidably mounted in the slots 68 and 69 is a top plate designated generally by the numeral 77 (FIG. 5) having a configuration substantially identical to the configuration of the base member 3 and plate 4, including peripheral edges 78 and 79 that converge toward the central axis 81, the top plate 77 thus being symmetrical with respect to the longitudinal axis 81. The top surface 82 of the top plate 77 is flat, as indicated, and extends forwardly to a forward mounting portion 83, and rearwardly to a mounting portion 84. The mounting portion 84, is provided with two oppositely projecting mounting lugs 86 and 87, and from each of the mounting lugs 86 and 87 there project in opposite directions in axial alignment pivot pins 88 and 89, each preferably fabricated from steel, and embedded in the associated lug 86 and 87. Centrally, the top plate 77 is provided with an egg-shaped aperture 91 similar to the aperture 36 in the base member 3, and of the same configuration. In like manner, the top plate 77 is provided with apertures 92, 93, 94 and 96, corresponding in placement when the top plate is mounted as illustrated in FIG. 1, so that the axes of the apertures 92–94 and 96 correspond to the axes of the apertures 37–39 and 41. On the opposite side of the longitudinal axis 81, there are corresponding apertures 93', 94' and 96', the purpose for these various apertures being to admit ejection pins to facilitate ejection of the hardened dental stone casting from the mold cavity as will hereinafter be explained.

Referring to FIG. 1, it will be seen that the underside of the top plate 77 viewed in the direction of the arrows 4—4 in FIG. 1, constitutes the mirror image of the surface 7 of the bottom plate 4. Thus, the top plate 77 is provided with an undersurface 97 from which project integral peripheral walls 98 here designated generally and collectively in the interest of brevity, with the understanding that the peripheral walls 98 include outer and inner peripheral walls joined at opposite ends by end walls to form a mold cavity 99 therewithin similar in configuration to the cavities 12 and 12' as illustrated in FIG. 4.

In the interest of brevity, it should be understood that the apertures 92–94 and 96 pass through the plate 77 in the same manner as the corresponding apertures in the bottom plate 4, with the three apertures 93, 94 and 96 being within the mold cavity 99. In like manner, it should be understood that the mold cavity 99 formed by the walls 98 is provided with a guide pin designated generally in FIG. 4 by the numeral 24. The guide pin passes through appropriate apertures formed in the front and rear walls of the cavity 99 as previously described with respect to lower plate 3 and cavity 12'.

As with the guide pin 24, the guide pin inserted through the cavity walls 98 is surrounded intermediate its ends and within the cavity 99 by a tubular plastic sleeve similar to the tubular sleeve 29 shown in FIG. 4. In the interest of brevity, it is noted that within the cavity 99, between the inner peripheral surfaces of the cavity walls 98 and the undersurface 97 of the plate 77 there are provided randomly spaced fillets of random width similar to the fillets 17 and 19 formed in the cavity 12 of FIG. 4 and for the same purpose. The random spacing of the fillets in the cavity 99 may or may not be similar to the random spacing of the fillets in the cavity 12. In like manner, the transverse width of the fillets in cavity 99 may or may not be the same as the transverse dimension of the fillets 17 and 19 in cavity 12 for the reason that each dental stone casting in each individual cavity is unique, and a casting originating from cavity 12 or 99, for instance, ought not be re-assembled with the other cavity.

Referring to FIG. 1, it will be seen that the top plate 77 is "articulable" in that it may be pivoted from a horizontal position as illustrated in FIG. 1 in full lines to a vertical position as illustrated in broken lines in FIG. 1. The pivotal axis is coincident with aligned axes of the pivot pins 88 and 89 pivotally journaled within the slots 68 and 69. It will thus be seen that the pivot pins are retained in the slots by driving the threaded set screws 74 amd 76 into the mounting portions 66 and 67 until the inner end of the set screws 74 and 76 project into the slots 68 and 69 with the pivot pins 88 and 89 pivotally located between the bottom of the slots, i.e., the inner ends of the slots, and the associated end of the set screws. It should be apparent that by gauging the depth of the slots 68 and 69 in relation to the axes of the set screws 74 and 76, the pivot pins 88 and 89 can be given sufficient clearance to slide transversely in addition to pivoting, thus enabling the top plate to "articulate" about a vertical axis in addition to being able to "articulate" about a horizontal pivotal axis. This lateral articulation is depicted in FIG. 16.

In this relationship, the top plate 77 may be pivoted into the position illustrated by broken lines in FIG. 1, and then swung downwardly again into the horizontal position illustrated in full lines. When necessary or desired, the portion 83 may be swung laterally within the limits permitted by the clearance between between the set screws and the pivot pins. However, when it is desired to remove the top plate 77 so as to replace it with another, the set screws 74 and 76 are backed out of the threaded bores, until the slot is clear of the obstruction formed by the inner ends of the set screws, and after pivoting the top plate 77 into its vertical position as illustrated in broken lines in FIG. 1, it may be removed by pressing it rearwardly in the direction of the arrow so that it now is free of the stanchion 49 as illustrated in broken lines in FIG. 1. Also, it should be noted that after the set screws are backed out of the slots, the top plate may be displaced rearwardly until the pivot pins clear the slots, and then the top plate may be elevated to remove it from the assembly.

Figure 2:
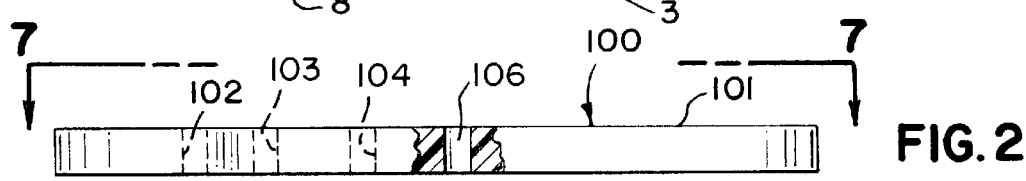
FIG. 2 is an edge elevational view of a spacer plate used in the process of casting a set of dentures in the apparatus of this embodiment. A portion of the spacer plate is broken away to illustrate one of a multiplicity of pin-receiving apertures that are formed in the spacer plate.

Referring to FIGS. 2 and 7, it will be seen that the spacer plate there shown constitutes another element of the combination forming the dental articulator apparatus of a first preferred embodiment described and illustrated herein. The spacer plate is designated generally by the numeral 100 and is symmetrical with respect to a longitudinal axis, one half of the plate being illustrated in plan in FIG. 7, being broken away medianly along the longitudinal center line as illustrated. The spacer plate includes a top surface 101 and is generally configured to underlie the base plate 4 of base member 3 and the top plate 77 in a manner and for a purpose which will hereinafter be explained. Formed in the spacer plate 100 is aperture 102 which lies on the central axis line of the plate, and apertures 103, 104, and 106 spaced apart and corresponding in position and spacing to the apertures 37–39 and 41 in FIG. 4. The other half of the plate (not shown) also includes corresponding apertures 103', 104' and 106' that are positioned for registry with apertures 42, 43 and 44 in FIG. 4 and complementary apertures in top plate 77 illustrated in FIG. 5. Stated another way, when the spacer plate 100 is slipped under the base plate 4 of base member 3, the apertures in the mold cavities discussed above will register with the corresponding apertures formed in the spacer plate 100. Like the base member 3 and the top plate 77, and the stanchion 49, the spacer plate 100 is conveniently formed from a tough synthetic resinous material, but may also be formed from any other suitable material, including metal.

Also forming a part of the dental articulator apparatus in this first embodiment is an ejector plate (FIG. 3) designated generally by the numeral 107 and including a flat plate having a thickness substantially twice the thickness of the spacer plate 100, and provided with seven steel pins 108, 109, 109' 112, 112' 113 and 113', the pins being distributed on the surface 114 of the plate 107 in a pattern corresponding to the pattern of the apertures 102, 103, 104 and 106 and the corresponding apertures 103', 104' and 106 (not shown) on the other half of the spacer plate 100, and corresponding also to the pattern of apertures in base plate 4 and top plate 77. The pins are press fitted into appropriate bores 116 formed in the plate 107, and extend perpendicular to the surface 114 of the plate for a distance that is equivalent to the thickness of the spacer plate 100 and the thickness of the base plate 4 of base member 3 and equivalent to the thickness of the spacer plate and the top plate 77. Thus, when the spacer plate 100 is superimposed over the ejector plate 107, the pins will project through the apertures in the spacer plate previously discussed, and will further project through the base member plate 4 (or the top plate 77) so that the top ends of the pins lie flush with the top surface 7 of the base plate 4 or the surface 97 of the top plate 77 when that plate is removed from the stanchion 49 in the manner previously described, and superimposed in an upside down position or relationship on the pin portions projecting from the ejector plate 107 and through the spacer plate. The reason for this relationship and the effect that it produces will be explained hereinafter in the discussion of the manner of operation of the apparatus of this first preferred embodiment.

Reference is now made to FIGS. 9 and 10. These figures illustrate alternate upper articulator plates that may be selectively substituted for the upper articulator plate 77 illustrated in FIGS. 1 and 5. Referring first to FIG. 9, the articulator plate is designated generally by the numeral 117 and includes a peripheral body portion 118 surrounding a central aperture 119 having an egg-shaped configuration similar to the apertures 36 and 91 in FIGS. 4 and 5, respectively. A mounting portion 121 having laterally extending mounting lugs 122 and 123 are provided with press-fitted steel pivot pins 124 and 126, respectively. The peripheral body portion 118 is provided with a forwardly projecting portion 127 similar to the projecting portion 32 that is useful in digitally manipulating the articulator plate.

Figure 4:
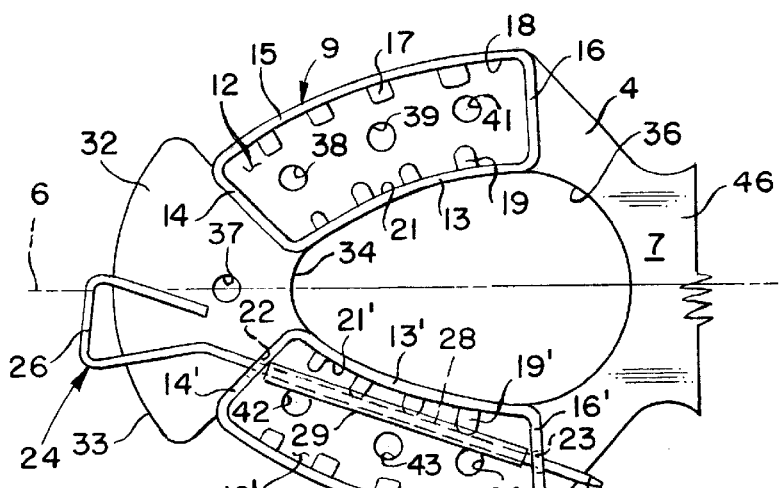
FIG. 4 is an elevational view in plan of the quadrant plate mold cavity plate taken in the direction indicated by the arrows 4—4 in FIG. 1, and shown detached from the support stanchion.
Figure 5:
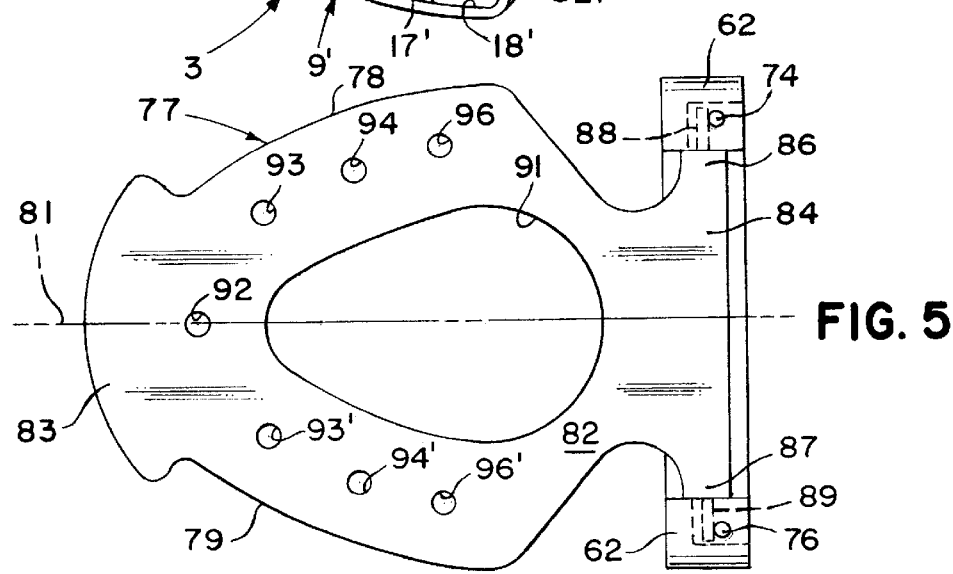
FIG. 5 is a top plan view of the top or maxillary mold cavity plate taken in the direction of the arrows indicated on the line 5—5 in FIG. 1.

In FIGS. 4 and 5, the casting cavities 12 and 12' are positioned on the surface 7 (97) of the plate 4 (77) in position to accommodate molars that might be found in the mouth of a patient. The structure in FIG. 9 distinguishes from the structure in FIG. 4 in that the cavity 128 is symmetrically positioned with respect to the central axis 129 and includes an inner peripheral wall 131 coinciding with the inner periphery of the aperture 119, at its small end, an outer peripheral wall 132 coincident with the outer periphery 133 of the front portion of the plate 118, and having end walls 134 and 136 closing the ends of the cavity generally in a position to include a quadrant containing the front teeth of a patient, perhaps including the canine teeth, the lateral incisors and the central incisors.

As with the plates illustrated in FIGS. 4 and 5, an aperture 137 is provided symmetrically positioned on the longitudinal axis 129 of plate 117 and within the cavity 128 as shown. This aperture 137 corresponds to the aperture 37 in FIG. 4 and aperture 92 in FIG. 5. In like manner, again referring to FIG. 9, within the cavity 128 there are formed two additional apertures 138 and 139, these latter apertures being on opposite sides of the central longitudinal axis 129 as shown. These apertures 138 and 139 correspond in position to the placement of apertures 38 and 42 in the plate 4 of FIG. 4, and the placement of apertures 93 and 93' in FIG. 5.

Within the cavity 128, again interposed between the inner periphery of the wall 131 and the surface of body portion 118, are a multiplicity of fillets 141 of random width that are randomly spaced, converging with the inner peripheral surface of the wall 131 and merging smoothly with the surface of body portion 118 constituting the bottom of the cavity 128 and the underside of the articulator plate 117. In like manner, the front peripheral wall 132 is provided with fillets 142 that are also randomly spaced and of random widths as indicated in the drawings. The fillets 142 merge smoothly with the inner periphery of the wall 132, and are intercepted by the surface of the body portion 118 which is coincident with the bottom surface of the cavity 128.

As explained in connection with the base member 3 incorporating mold cavity plate 4 as illustrated in FIG. 4, the plate 117 in FIG. 9, and specifically the front peripheral wall 132 of cavity 128 is provided with aligned apertures 143 and 144, that are disposed generally medianly between the arcuate top edge of the front peripheral wall 132, and which aligned apertures receive therethrough a guide structure designated generally by the numeral 146 and including a guide pin 147 having an intermediate portion 148, and a terminal portion 149, the intermediate portion 148 being surrounded by a synthetic resinous tube or knurled sleeve 150 that extends chord-like across the concave curvature of the peripheral wall 132. The guide structure 146 cooperates with the fillets 141 and 142 to accurately re-position and retain in the cavity in which it was formed, a stone-formed replica of a patient's teeth or tooth for use by the dental technician for reconstructing an artificial crown for an already existing tooth.

Referring to FIG. 10, this alternate articulator plate is intended to be used when a full impression of all of the teeth in a patient's mouth has been provided to the dental laboratory by a dentist. This plate is designated generally by the numeral 151 and includes a surface 152, a mounting portion 153 opposite ends of which provide oppositely extending mounting lugs 154 and 156. The mounting lugs 154 and 156 receive, respectively, press-fitted pivot pins 157 and 158. The articulator plate 151 obviously has the same configuration as the articulator plate 117 illustrated in FIG. 9, including the shape of the central aperture 159 and the forwardly projecting portion 161 that lies symmetrically on opposite sides of the central axis 162.

Projecting from the surface 152 of the articulator plate 151 is a casting cavity designated generally by the numeral 163 and defined by an arcuate inner peripheral wall 164, an outer peripheral wall 166 substantially parallel to the inner wall, and end walls 167 and 168. It will be noted that the inner peripheral wall 164 of the cavity 163 generally conforms to a major portion of the inner peripheral surface of the central aperture 159. In like manner, the outer peripheral wall 166 of the cavity conforms in large part to the generally curved outer peripheral surface 169 of the articulator plate 151. It should be noted that the end walls 167 and 168 lie in a common transverse plane and are provided with centrally positioned apertures 171 and 172, respectively.

Complementing the apertures 171 and 172 are apertures 173 and 174 formed in the curved front portion of the outer peripheral wall 166. Inserted through the corresponding apertures 171/173 is a guide structure designated generally by the numeral 176 and including an elongated guide pin 177 that extends through the apertures 171 and 173 and through a surrounding tubular synthetic resinous sleeve 178. In like manner, the apertures 172/174 receive the insertion of a similar guide structure designated generally by the numeral 179 and including an elongated guide pin 181 surrounded within the cavity 163 by a tubular sleeve 182.

In this alternate portion of the apparatus, there is provided a third guide structure designated generally by the numeral 183 and, like the guide structures 176 and 179, the guide structure 183 passes chord-like through the cavity 163 through apertures 184 and 186 formed in the outer peripheral wall 166 of the cavity as shown. An intermediate guide pin portion 187 is provided within the cavity surrounded by a tubular synthetic resinous knurled sleeve 188, as previously discussed, which extends chord-like across the cavity and having ends that abut the inner peripheral surface of the outer peripheral wall of the cavity. These guide structures are illustrated in FIGS. 4, 9 and 10 to illustrate the positions in which they will be used during the process of forming a replica of a patient's tooth structure or teeth. As previously discussed, the guide pins cooperate with a segmented dental casting and the cavity in which it was formed to retain the casting segments precisely in their original positions in which they were cast.

As with the articulator plates previously described, the articulator plate 151 is also provided with a series of apertures beginning with a centrally positioned aperture 189 that lies on the central axis and within the cavity 163 generally medianly between the inner and outer peripheral walls as shown. Three additional apertures corresponding in size and placement to similar apertures previously described in the other articulator plates are provided on the left side of the central axis 162. These are numbered 191, 192 and 193. Similar apertures are formed in the plate 151 on the right side of the central axis 162 and these are numbered 194, 196 and 197 as shown. All of these seven apertures on the left and right sides of the central axis 162 lie within the definition of the cavity 163 as shown.

The dental articulator apparatus described above is used by a dental laboratory and a dental technician working for that laboratory to reproduce one or more dentures for a dentist, or to prepare a crown for an existing tooth in the mouth of a patient. The procedure commences with the dentist utilizing a special powdered substance that is mixed with an appropriate solvent to provide an initially soft paste-like material that is deposited in a dental tray. The dentist then presses the open end of the tray filled with the hardenable rubberized plastic against the teeth of which he wants to make an impression, and the patient is usually requested to close his mouth or apply soft pressure on the tray. The tray is left in the patient's mouth for approximately five minutes or until the rubberized plastic hardens, and thereby creates in the hardened mass an exact "negative", i.e., depressions, that exactly match the patient's teeth. After about five minutes, the dentist removes the tray containing the now hardened "Alginate" which has impressed itself into the exact configuration and location of the patient's teeth.

This "Alginate" impression is now dispatched to a dental laboratory for production in dental stone, a type of cementitious material used for this purpose, of an exact "positive" of the patient's teeth as provided by the "negative". It is for this purpose that the dental articulator apparatus described above is used.

When the impression is received from the dentist at the dental laboratory, accompanied by instructions from the dentist with respect to what type of work the dental laboratory must perform, a dental technician mixes up a quantity of dental stone into a relatively soft moldable paste and fills the cavities in the impression received from the dentist. To insure that every crevice contained within the impression is filled with the paste-like stone material, it is preferred that the impression, with paste material now filling the voids forming the impression, be vibrated in order to eliminate any air bubbles that might be contained within the still paste-like plastic stone mixture. This requires only a short time, say a minute or two, and it insures that the end product to be removed from the impression will be an exact replica of the patient's teeth. Following vibration of the paste-filled impression, the same type of dental stone is deposited in one or more of the cavities.

Figure 11:
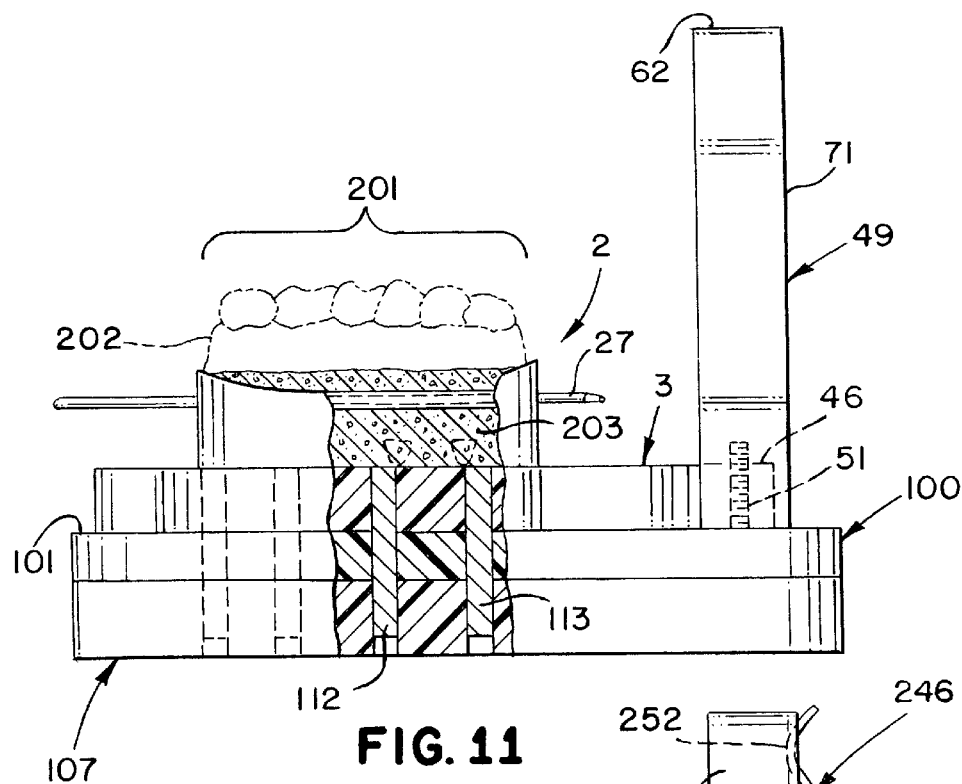
FIG. 11 is a fragmentary elevational view partly in vertical section of the lower or base casting plate attached to the upright stanchion with the base plate supported on the intervening apertured spacer plate which is in turn mounted on the ejector plate, this assembly shown in relation to a dental casting contained in the mold cavity with portions of the structures broken away to reveal underlying structural relationship of the elements assembled to receive the "plastic" dental stone in the casting cavity.

In preparation for filling a mold cavity with the paste-like moldable dental stone, the guide structure 24 (FIG. 4) is mounted in the cavity by digitally inserting or holding within the cavity the appropriate length of tubing 29. The end 27 of the guide pin is then slidably inserted through the aperture 22 and slidably threaded through the interior of the tube 29 having a knurled outer surface as seen in FIG. 16, with the distal end of the guide pin projecting through the aperture 23. In this first embodiment, apertured spacer plate 100 illustrated in FIGS. 2 and 7 is now deposited onto the ejector plate 107 so that the ejector pins project snugly through the apertures in the spacer plate. This relationship is illustrated in FIG. 11. Now, the articulator plate 3 is superimposed over the spacer plate 100 so that the pins 108, 109, 112 and 113 (FIG. 3) project into the apertures 37, 38 and 41 as illustrated in FIG. 4, and into the apertures 42, 43 and 44. It will be seen from FIG. 11, that this places the top ends of the pins flush with the bottom surface of the cavity 12', thus plugging those apertures.

The plastic and moldable dental stone is now deposited into the cavity so that it fully surrounds the intermediate portion of the guide pin and the surrounding knurled plastic tubing 29 and fills the cavity. The impression received from the dentist, having been filled with wet and plastic dental stone, is now inverted and arranged in superposed relationship on the dental stone-filled cavity so that the plastic and moldable dental stone within the cavity intermingles with the plastic and moldable dental stone with which the impression is filled. The stone-filled dental impression superimposed onto the stone-filled cavity 12 is left there for approximately ten to forty minutes until the dental stone hardens into a homogeneous and monolithic block of stone including the projection of the now hardened stone into the cavities of the impression to form in stone the exact size, location and configuration of the patient's teeth.

Referring to FIG. 11, it will be seen that when the combined dental stone assembly borne by the dentist's impression and that in the cavity has hardened after ten to forty minutes, the relatively flexible dentist's impression material sold under the trademark "Alginate" may be "stripped" from the now formed and hardened dental crown piece designated generally by the numeral 201. The crown piece constitutes an exact reproduction of the patient's tooth pattern and gum outline designated generally by the numeral 202, now joined in one homogeneous monolithic mass with the hardened dental stone body 203 filling the cavity in the articulator plate, and being formed along its lower peripheral edges with position locating recesses 204 that "key" the stone casting, or individual segments thereof, to precisely the same position when the casting is replaced in the mold cavity after having been ejected therefrom.

To remove or eject the now hardened stone crown casting 201 from the casting cavity, the articulator plate bearing the crown casting is lifted and separated from the pins of the ejector plate with the guide pin and tubular plastic sleeve still in place. Next, in this first embodiment being described, the spacer plate 100 is removed from the pins of the ejector plate 107 and set aside for use in connection with another casting. The ejector plate 107, now devoid of the spacer plate 100, is now in condition to again receive the articulator plate 3, which is now superimposed over the ejector pins projecting from the ejector plate 107, so that the pins project into the apertures formed in the articulator plate cavity and impinge lightly against the bottom of the casting. In this embodiment, it should be noted that in this intermediate relationship, in the absence of the spacer plate, a space 205 exists between the lower surface of the articulator plate and the top surface of the ejector plate. This assembly of ejector plate and articulator plate with the casting in place is then transferred to the press device illustrated in FIG. 12 and designated generally by the numeral 206. Alternatively, the ejector plate may first be associated with the press device and the articulator plate then mounted on the pins of the ejector plate.

Prior to attempting to eject the now hardened crown casting 201 from the casting cavity, it is necessary that the guide pin 24 be removed from the articulator plate and casting. This is effected by grasping the handle end 26 of the guide pin, rotating it slightly and tugging to withdraw it from the interior of the plastic tubing 29. The plastic tube remains embedded in the casting and is prevented from being rotated or withdrawn from the crown casting by the knurling on the exterior surface of the tubing. This operation may be performed either prior to or after the ejector plate/articulator plate assembly is placed in the press.

Figure 12:
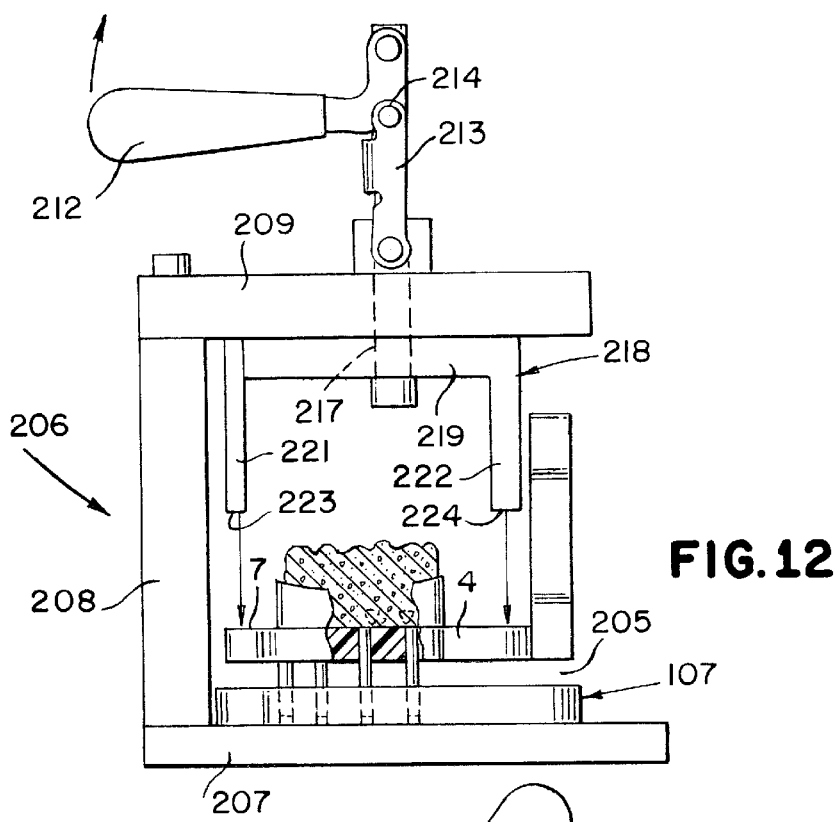
FIG. 12 is a side elevational view of an ejector press frame on the base of which the ejector plate of FIG. 3 is mounted, with the guide pin and spacer plate of FIG. 2 removed and the articulator base plate superimposed over the pins of the ejector plate, in preparation of ejecting the dental casting from the mold cavity by imposing a downwardly directed force on the articulator base plate.
Figure 13:
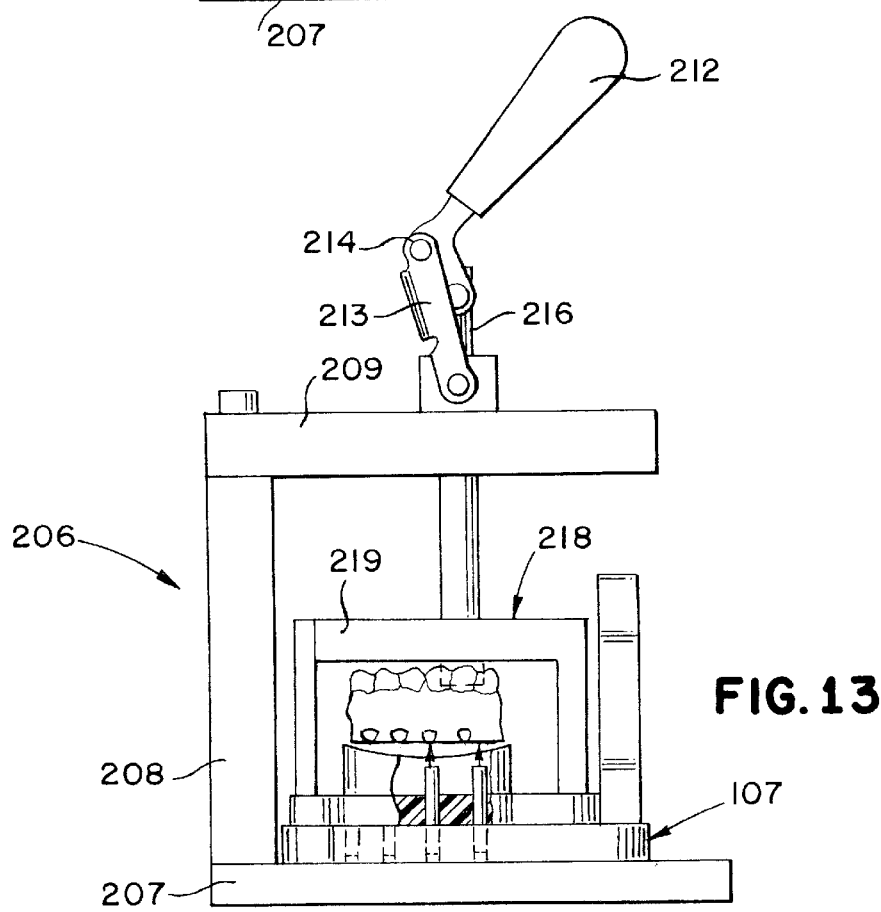
FIG. 13 is a view similar to FIG. 12, but showing the articulator base plate pushed downwardly by manipulation of the press so as to cause the ejector pins to project upwardly into the mold cavity to eject the dental casting from the mold cavity.

The press includes a base 207, preferably of steel, an upright stanchion 208 also of steel connected at its lower end to the base 207 and at its upper end provided with a steel cantilever beam 209 spaced above and extending in the same direction as the base. The beam 209 extends substantially parallel to the base 207, the width and length of which is sufficient to receive and support the ejector plate 107. Mounted on the beam 209 is a handle 212 connected to a levered toggle mechanism 213, one lever of the toggle having one end 214 pivotally connected to the upper end of a slide shaft 216. The slide shaft 216 passes through the cantilever beam 209, and on its free end 217 below the cantilever beam 209, the slide shaft has mounted thereon a generally U-shaped steel yoke designated generally by the numeral 218 and including a cross-beam 219 from opposite ends of which integrally depend downwardly projecting legs 221 and 222. The length of the downwardly projecting legs 221 and 222 are such that the lower surfaces 223 and 224 of the legs come into contact with the top surface of the articulator plate when the handle 212 is swung clockwise to the right as seen in FIG. 12 so as to cause the toggle to drive the slide shaft downwardly. Continued clockwise manipulation of the handle 212 into the position illustrated in FIG. 13, causes the legs 221 and 222 to press the plate 4 downwardly on the pins, causing the upper ends of the stationary pins to press with force against the bottom of the monolithic stone casting 203, thereby eliminating the space 205 and causing the casting to be ejected from the interior of the mold cavity. This condition is illustrated in FIG. 13. The monolithic stone casting may now be cut into segments as illustrated in FIG. 25, and the segments re-assembled as in FIG. 26 by re-insertion of the guide pin, or the segments may be re-assembled in the cavity and then the guide pin re-inserted through the segments as in FIG. 28.

The embodiment of the invention described above and illustrated in FIGS. 1–13 embodies many of the aspects that are embodied in the second embodiment of the invention that is illustrated in FIGS. 14–28. For instance, with respect to the articulator plates illustrated in FIGS. 4, 5, 9 and 10, the description above relating to the formation of the mold cavities on these plates, the formation of the fillets between the inner peripheral surfaces of the mold cavity walls and the bottom surface of the cavity, and the placement of the guide pin or guide structure which extends through the cavity and impales the elongated tubular sleeve, are all replicated in the second embodiment of the invention illustrated in FIGS. 14–28.

Figure 14:
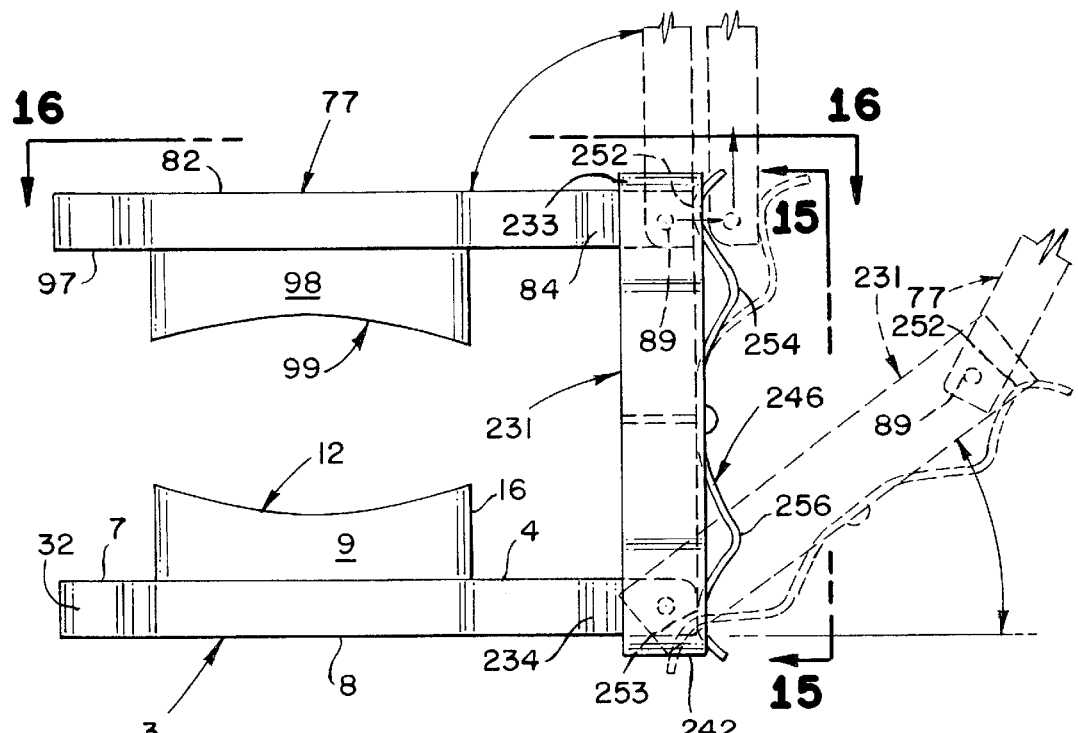
FIG. 14 is a side elevational view similar to FIG. 1, but illustrating a second preferred embodiment of the dental articulator apparatus having upper and lower mold cavities that are pivotally and slidably mounted in relation to the stanchion plate and resiliently retained in operative position.
Figure 15:
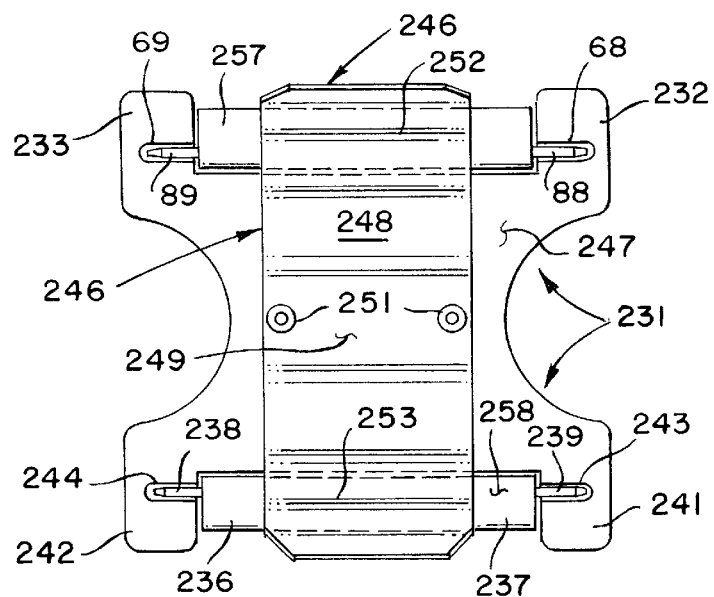
FIG. 15 is a rear elevational view of the assembly of stanchion plate, upper maxillary mold cavity plate, lower mandibular mold cavity plate, and the resilient means for retaining the assembly in operative condition. The view is taken in the direction of the arrows on the line 15—15 in FIG. 14.
Figure 20:
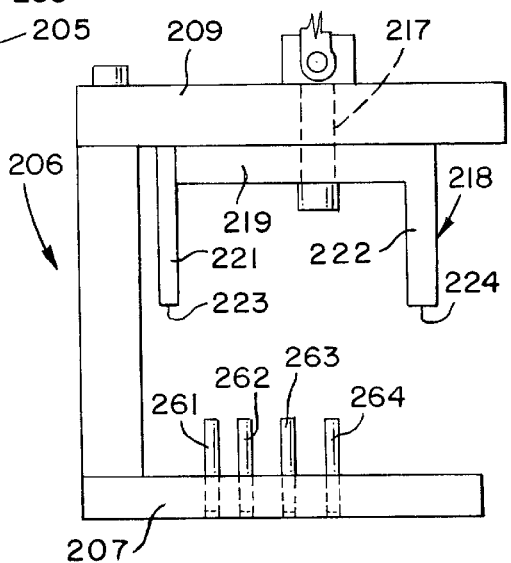
FIG. 20 is a side elevational view of the ejector press frame of the second preferred embodiment. A portion of the structure is broken away.

The differences that exist between the two embodiments that are described and illustrated herein reside primarily in the manner in which the articulator plates are mounted to the support stanchion, and these differences are illustrated in FIGS. 14–16 which relate to the second embodiment of the invention. An additional difference in this second embodiment is elimination of the spacer plate illustrated in FIG. 2 which relates to the first embodiment described above, and the combination of the ejector plate illustrated in FIG. 3 with the base 207 of the press device illustrated in FIG. 13 of the first embodiment to arrive at the press structure illustrated in FIGS. 20–22, inclusive, wherein the ejector pins as described above with respect to the embodiment illustrated in FIGS. 1–13 are part of the base of the press device as illustrated in FIG. 20.

In the interest of brevity in this description, where the structure in the second embodiment is essentially a replication of the structure in the first embodiment, the same reference numbers have been applied to the structure illustrated in FIGS. 14–28. Where the structure differs significantly in this second embodiment from the structure illustrated and described in the first embodiment, separate reference numbers have been utilized to indicate that different structure.

Accordingly, referring to FIGS. 14 and 15 which illustrate the second embodiment, it will be noted that the upper articulator plate 77 remains the same in structure and function as the articulator plate 77 illustrated in FIGS. 4 and 5. In like manner, the lower articulator plate 3 illustrated in FIG. 14 is a replication of the articulator plate 3 illustrated in FIG. 1. The differences in structure, function and mode of operation embodied in second preferred embodiment FIGS. 14–17 relate to the manner and means by which the lower articulator plate 3 and the upper articulator plate 77 are jined to the modified stanchion 231 of the second preferred embodiment that supports the two articulator plates albeit in a different manner.

Thus, in both embodiments, the articulator plates are provided with mounting portions, the lower articulator plate 3 having a reconfigured mounting portion, while the upper articulator plate 77 is provided with a mounting portion 84 as before. The mounting portion 84 is similarly provided in the second embodiment with oppositely extending mounting lugs 86 and 87 (FIG. 17) in which are press-fitted oppositely extending pivot pins 88 and 89. These pivot pins extend slidably into transverse slots 68 and 69 (FIGS. 15 and 16) formed in modified monolithic stanchion 231 mounting portions 232 and 233, respectively, in the same manner as is illustrated in FIG. 6.

The modified stanchion 231 in FIGS. 14–17 is slotted in the same manner as its upper end as illustrated in FIG. 6, and the pivot pins 88 and 89 extend into those transverse slots 68 and 69 in the same manner as previously described in connection with the structure illustrated in FIG. 6. It should be noted however that in this second embodiment the threaded bores 72 and 73 and the complementary set screws 74 and 76 are omitted and a different articulator plate retention means is provided as will hereinafter be explained. Also, aperture 59 formed in the stanchion 49 is omitted in this second embodiment stanchion 231.

Additionally, in this second embodiment of the invention, at the base of the stanchion 231 as shown in FIGS. 14–17, the lower articulator plate is modified to reconfigure the mounting portion 46 as illustrated in FIGS. 1 and 6 to provide a modified mounting portion 234 (FIGS. 14 and 17) having laterally and oppositely extending mounting lugs 236 and 237 (similar to mounting lugs 86 and 87 of the upper articulator plate). Press-fitted into the mounting lugs 236 and 237 are pivot pins 238 and 239 similar to pivot pins 88 and 89 of the first embodiment as illustrated in FIG. 6. Modified stanchion 231 is provided with mounting portions 241 and 242 similar to mounting portions 232 and 233, and these mounting portions are provided with slots 243 and 244 (similar to slots 68 and 69 formed in mounting portions 232 and 233) and into which the pivot pins 238 and 239 extend.

To resiliently, pivotally and detachably mount the upper and lower articulator plates on the support stanchion, there is provided resilient means designated generally by the numeral 246 mounted on the rear surface 247 of the support stanchion. The resilient means is in the form of an elongated spring metal band 248 symmetrical about its longitudinal axis and having a central body portion 249 that is retained tightly against the central portion of the rear surface 247 by appropriate fastening means such as screws 251.

The spring metal band is formed at opposite end portions on opposite sides of the central body portion and adjacent each end thereof with transversely extending arcuate bearing portions 252 and 253. Intermediate the central body portion and the arcuate bearing portions, the spring metal band is formed to provide intermediate arcuate portions 254 and 256 which are spaced from the rear surface of the support stanchion as shown in FIG. 14, and which are therefore displaced from the plane of the central body portion.

Preferably, the convex surface of the arcuate bearing portion 252 is in line contact with the associated end edge 257 of the articulator plate 77 when the articulator plate projects perpendicularly from the stanchion plate as llustrated in FIG. 14. In that relationship, the line contact between the arcuate bearing portion and the end edge 257 is coincident with a horizontal plane that also includes the pivotal axis provided by the pivot pins 88 and 89.

In like manner, referring now to the pivotal and slidable relationship between the lower articulator plate 3 and the associated end of the support stanchion, again referring to FIG. 14, it will be seen that the arcuate bearing portion 253 of resilient means 246 bears in line contact against the end edge 258 of mounting portion 234 of lower articulator plate 3. Preferably, the line contact is coincident with a plane that also includes the pivotal axis provided by pivot pins 238 and 239.

It will thus be seen that the resilient means 246 retains the articulator plates 3 (lower) and 77 (upper) of this second embodiment pivotally yet detachably mounted on the stanchion 231 in a manner to provide the quality or characteristic of "centricity" that enables the upper and lower articulator plates to be displaced laterally in relation to one another (as shown in broken lines in FIG. 16) to accommodate missaligned confronting occlusal surfaces, and yet be returned to a "centric" position as illustrated in full lines in FIG. 16 by virtue of the bias imposed on the articulator plates by impingement thereon of the arcuate bearing portions 252 and 253. In this respect, as illustrated in FIG. 16, lateral displacement of the forwardly projecting portion of the base plate of the articulator plate will cause one or the other of the pivot pins (88, 89, 238 or 239) to slide away from the bottom of the slot in which it is contained, the opposite pivot pin and the associated bottom of that slot acting as the fulcrum about which the articulator plate pivots laterally.

Importantly, in addition to lateral pivotal displacement as seen in FIG. 16, both articulator plates 3 and 77 are enabled to pivot about the axes of the aligned pivot pin sets 88/89 and 238/239. This type of pivotal displacement of the articulator plates is partially shown in broken lines in FIG. 14 where it is shown that the modified support stanchion 231 is pivoted clockwise about the pivot pins 238 and 239, while the upper articulator plate 77 is pivoted in relation to the support stanchion on the aligned pivot pins 88 and 89. It will of course be apparent from FIG. 17 that continued clockwise rotation of the support stanchion 231 and the upper articulator plate 77 will bring the structural elements of the assembly into the attitude illustrated in FIG. 17 wherein the support stanchion lies horizontally, and the two articulator plates 3 and 77 extend horizontally from opposite ends of the support stanchion, so that all three elements of the assembly lie in essentially a common plane as shown.

A still further advantage of this construction of the articulator assembly is that each of the articulator plates 3 and 77 may be individually detached from the support stanchion merely by extending the lateral displacement of the articulator plate as shown in FIG. 16 until one of the pivot pins is displaced out of the slot in which it normally lies. To accomplish this, the associated arcuate bearing portion of the spring metal band 248 is resiliently displaced in a direction away from the rear surface of the support stanchion by the laterally directed force imposed on the articulator plate until the pivot pin clears the slot and rests on the rear surface of the stanchion adjacent the slot from which it has been extracted. A slight rearward force imposed on the articulator plate will now press the associated end of the arcuate bearing portion rearwardly, thus clearing the opposite pivot pin from its slot, whereupon the articulator plate may be removed from the stanchion.

Figure 3:
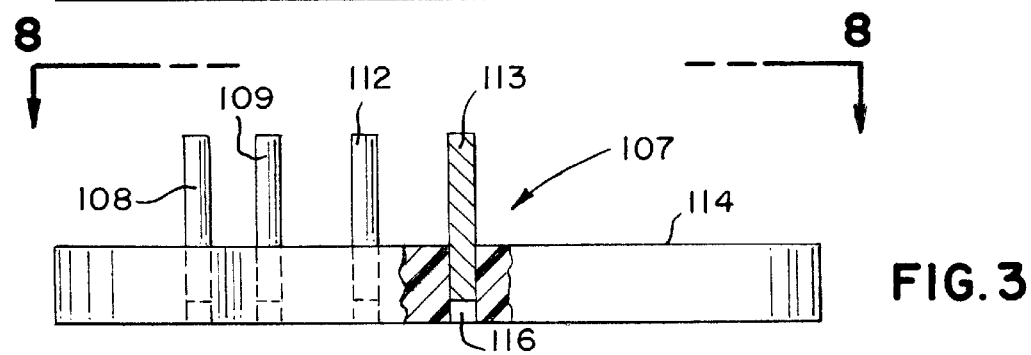
FIG. 3 is an edge elevational view of the press ejector plate utilized to eject the hardened dental stone casting from the mold cavity in this first preferred embodiment.
Figure 21:
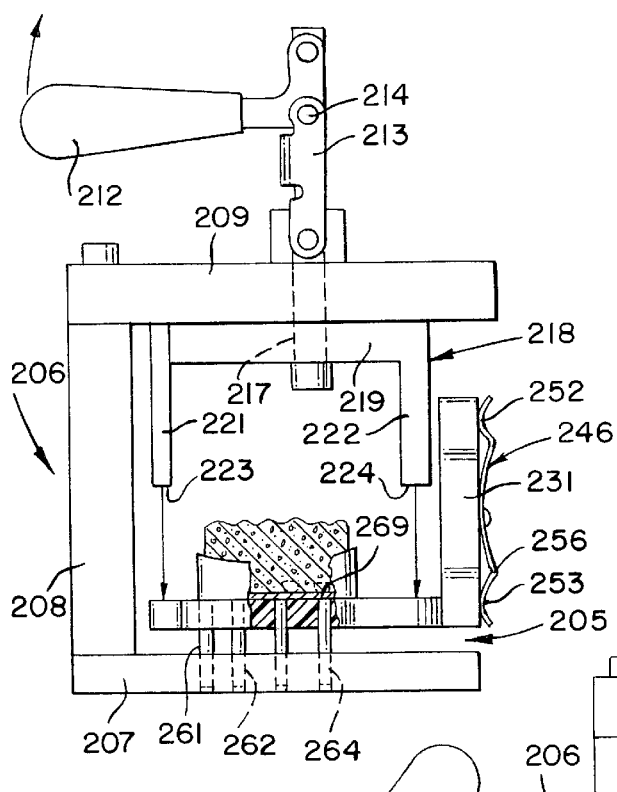
FIG. 21 is a side elevational view of the second embodiment ejector press frame, with the mold cavity plate of FIG. 18 superimposed on the ejector pins in preparation of ejecting the dental casting.
Figure 22:
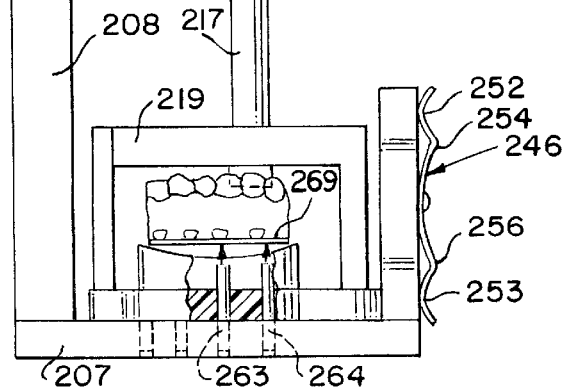
FIG. 22 is a view similar to FIG. 21, but showing the press apparatus manipulated to press the mold cavity plate downwardly to cause the ejector pins to penetrate into the mold cavity to eject the hardened "positive" tooth casting from the mold cavity.

Comparing to FIGS. 2, 3 and 11 of the first embodiment with FIGS. 18–22 of the second embodiment, it will be noted that in the second embodiment the spacer plate 100 and the ejector plate 107 in which are mounted the seven ejector pins have both been eliminated. In this second embodiment, the base 207 of the press device is itself provided with seven ejector pins, four of which ejector pins 261, 262, 263 and 264 are illustrated in FIGS. 20–22, the remaining three ejector pins 266, 267 and 268 being in alignment behind the pins 261, 262 and 263, and therefore not visible in these views. Suffice to say that the seven ejector pins are press-fitted into the base 207 of the press device in a pattern of distribution to conform to the pattern of distribution of the apertures 37, 38, 39, 41, 42, 43 and 44 shown in FIG. 4, and conforming also to the pattern of distribution of the apertures 92, 93, 94, 96, 93', 94' and 96' shown in FIG. 5. In like manner, the pattern of distribution of the seven ejector pins press-fitted into the base 207 of the press device 206 conform to the pattern of distribution of the apertures formed in the articulator plates 117 and 151 illustrated in FIGS. 9 and 10, thus enabling universal application of the press device with the various articulator plates illustrated and described herein.

Because of the elimination of the spacer plate 100 and the ejector plate 107, the ejector pins press-fitted into the base 207 need not be as long as the ejector pins utilized in the first embodiment in which the upper ends of the pins functioned to form a plug so that plastic dental stone did not pass into the apertures that normally opened into the casting cavity. Thus, referring to FIGS. 18, 19, 21 and 22, it will be seen from FIGS. 18 and 19 that in this second embodiment, a cavity floor plate 269 of thin yet rigid material, preferably stainless steel, is configured to conform to the configuration of the bottom of the cavity, including recesses to accommodate the fillets previously discussed. The cavity floor plate fits snugly into the cavity, and functions to prevent plastic dental stone from entering the apertures formed in the bottom of the cavity forming a part of the articulator plate. The cavity floor plate is partially illustrated in cross-section in FIG. 18, and is illustrated in cross-sectional plan in FIG. 19.

Figure 18:
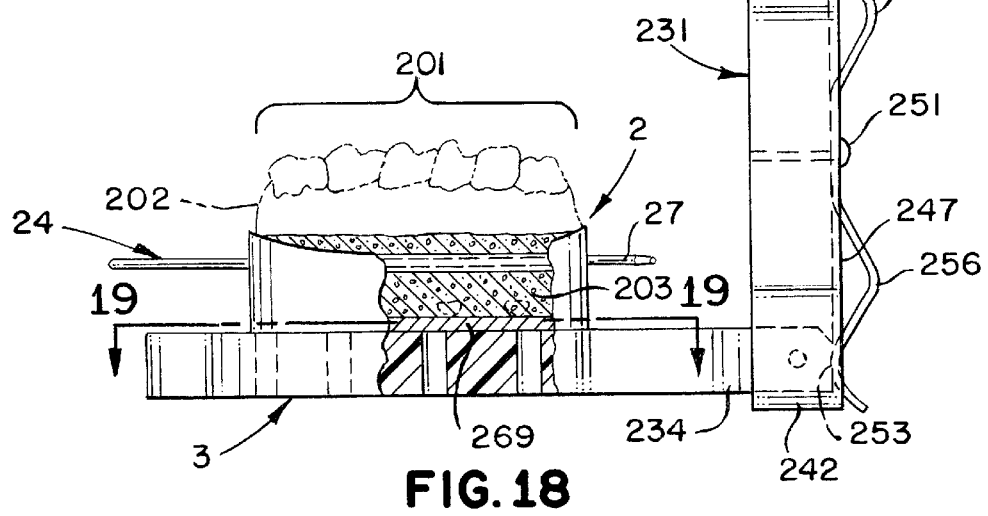
FIG. 18 is a fragmentary elevational view of the lower mandibular mold cavity plate of FIG. 14, showing the formation of the hardened dental stone and placement of the guide rod. Portions of the structure are broken away to reveal underlying structure, and the upper maxillary articulate plate is removed.
Figure 19:
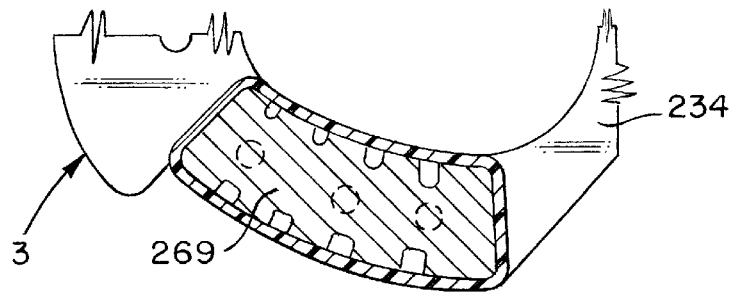
FIG. 19 is a horizontal sectional view taken in the plane indicated by the line 19—19 in FIG. 18 and in the direction indicated by the arrows.

Thus, with a cavity floor plate inserted in each cavity into which plastic dental stone is to be cast, the dental stone hardens and the cavity floor plate sticks to the underside of the hardened body of dental stone. This relationship is illustrated in FIG. 18. When it is desired to press the now hardened dental casting from the cavity, the articulator plate is superimposed over the ejector pins as illustrated in FIG. 21 so that the ejector pins penetrate the bores in the articulator plate, with the upper ends of the ejector pins impinging lightly against the underside of the cavity floor plate 269. Manipulation of the press device by swinging the handle clockwise as shown in FIG. 22 now imposes a downwardly directed force on the articulator plate, causing it to be displaced downwardly so that the ejector pins project through and beyond the articulator plate, pushing upwardly on the cavity floor plate with resultant upward displacement of the now hardened dental casting as illustrated in FIG. 22. It will of course be understood, as previously discussed in connection with the first embodiment, that prior to filling the cavity with plastic dental stone, the guide pin and its surrounding tubular sleeve are positioned in the cavity so that the tubular sleeve and guide pin lie embedded in the dental stone when it hardens. In like manner as previously described, prior to ejecting the hardened casting from the cavity, the guide pin is withdrawn, leaving the tubular sleeve embedded in the stone casting.

In FIGS. 21 and 22, the support stanchion 231 is shown still attached to the articulator plate being pressed to eject the dental casting. It should of course be understood that the apparatus may of course be used in this manner, or alternatively, the stanchion by be pivoted in relation to the articulator plate in the manner previously discussed, and as illustrated in FIG. 14. In this latter orientation, the stanchion may be used as a handle to properly place the articulator plate in superimposed relation to the ejector pins as illustrated in FIG. 21. It will thus be seen that in this second embodiment of the invention, either or both articulator plates may be superimposed on the ejector pin pattern without detachment from the support stanchion, or each of the articulator plates may be detached from the stanchion as previously disussed, prior to either of the the articulator plates being inserted into the press device and superimposed over the ejector pins in preparation for ejection of the dental stone casting from the mold cavity in which it has hardened.

Having described the invention, what is believed to be new and novel and sought to be protected by Letters Patent of the United States is as follows.

We claim:

1. A dental articulator apparatus for use in the fabrication of artificial dentures, comprising:

a) a monolithic dental articulator mold plate support stanchion;

b) at least one dental articulator mold plate articulatively mounted on said monolithic support stanchion;

c) wherein said monolithic support stanchion is provided with at least one integral base portion, and said at least one dental articulator mold plate includes a mounting portion articulatively mounted on said at least one base portion of said support stanchion;

d) said at least one base portion of said support stanchion is provided with a pair of slots coincident in a common plane, said mounting portion of said at least one articulator plate includes a pair of axially aligned and spaced pivot pins, said aligned pivot pins being detachably engaged in said pair of slots;

e) means mounted on said support stanchion selectively retaining said aligned pivot pins in said pair of slots, whereby said at least one articulator plate is selectively articulatable transversely from a centered position to a laterally offset position and selectively articulatable about the axis of said pivot pins into a plane substantially coincident to the plane of said support stanchion;

f) said means selectively retaining said aligned pivot pins in said pair of slots comprises spring means mounted on said support stanchion and impinging on said at least one dental articulator plate and imposing a biasing force thereon to normally retain said pair of pivot pins pivotally and slidably engaged in said pair of slots while enabling selective removal of said at least one dental articulator plate from said support stanchion;

g) said support stanchion is provided with two opposed base portions;

h) two spaced confronting dental articulator plates are provided, each including a mounting portion normally pivotally mounted on an associated one of said opposed base portions of said support stanchion, each of said two spaced dental articulator plates including a base plate;

i) at least one mold cavity integrally formed on each base plate, said at least one mold cavity including side and end walls projecting perpendicularly from the associated base plate to provide free edges spaced from the associated base plate;

j) at least one pair of spaced aligned apertures formed in selected walls of said at least one mold cavity and spaced from said base plate;

k) a guide pin extending through said aligned apertures and across said cavity;

l) a sleeve slidably surrounding said guide pin between said selected cavity walls;

m) a plurality of randomly spaced fillets within said mold cavity merging smoothly between said side walls and said base plate;

n) a plurality of apertures formed in the bottom of each said mold cavity and penetrating through said base plate;

o) means closing said plurality of apertures in the bottom of each said mold cavity whereby dental stone having the quality of plasticity and filling said mold cavity is precluded from entering said plurality of apertures; and p) press means cooperably adapted to receive a dental articulator plate in the mold cavity of which a mass of dental stone has hardened and selectively manipulable to eject said hardened mass of dental stone from said mold cavity.

2. A dental articulator apparatus according to claim 1, wherein
   a) said mans closing said plurality of apertures comprises an ejector plate having a plurality of ejector pins therein corresponding in spacing with said plurality of apertures in each said dental articulator plate; and
   b) a spacer plate having a plurality of apertures substantially corresponding in diameter and spacing with said apertures in said dental articulator plate;
   c) whereby when said spacer plate is superimposed on said ejector plate and said dental articulator plate is superimposed on said ejector plate pins and said spacer plate the ends of said pins remote from said ejector plate lie flush in the bottom of said mold cavity to thereby preclude entry into said dental articulator plate apertures plastic dental stone deposited in said mold cavity.

3. A dental articulator apparatus according to claim 2, wherein said ejector plate is generally flat and said ejector pins correspond in length to the thickness of said spacer plate plus the thickness of said dental articulator plate.

4. A dental articulator apparatus according to claim 1, wherein said closing said plurality of apertures in said mold cavity comprises a thin plate conforming to the inner periphery of said mold cavity and superimposed over the bottom of said mold cavity and the apertures therein.

5. A dental articulator apparatus according to claim 1, wherein
   a) said press means comprises a base plate;
   b) a stanchion plate mounted by one end on said base plate and extending perpendicularly therefrom;
   c) a cantilever beam mounted on the end of said stanchion plate remote from said base plate;
   d) force exerting means mounted on said cantilever beam including a shaft slidably disposed in said cantilever beam;
   e) a handle pivoted on said shaft above said cantilever beam;
   f) a toggle mechanism operatively interposed between said cantilever beam and said handle whereby selective manipulation of said handle effects axial translation of said shaft; and
   g) a force exerting head mounted on the end of said shaft remote from said handle for selectively imposing a compressive force on a dental articulator plate superimposed on the pins of said ejector plate to thereby eject said hardened mass of dental stone from said mold cavity.

6. A dental articulator kit for use by a dental technician for replicating in dental stone a "positive" tooth pattern from a "negative" tooth pattern provided by a dentist, said dental articulator kit comprising:
   a) a support stanchion having first and second opposing end edges;
   b) a mandibular dental articulator plate having upper and lower surfaces and at least one mold cavity integrally formed on said upper surface, said mandibular dental articulator plate being mounted on one of said opposing end edges of said support stanchion;
   c) a maxillary dental articulator plate having upper and lower surfaces and at least one mold cavity integrally formed on said lower surface, said maxillary dental articulator plate being mounted on the other of said end edges of said support stanchion whereby said mold cavities on said mandibular and maxillary dental articulator plates may be selectively disposed in confronting relation;
   d) an ejector plate having a plurality of ejector pins arranged in an arcuate series and manipulable to eject said "positive" dental stone replica cast in one of said mold cavities;
   e) a spacer plate having a plurality of apertures arranged in an arcuate series complementing in number and placement said arcuate series of ejector pins on said ejector plate; and
   f) press means including a base plate adapted to support said spacer plate and selectively manipulable when one or the other of said dental articulator plates is superimposed over said spacer plate and said ejector plate to cause said ejector pins in said ejector plate to eject a "positive" dental stone replica cast in said one or the other of said mold cavities.

7. A dental articulator kit as described in claim 6, wherein said mold cavities integrally formed on said mandibular and maxillary dental articulator plates are defined by side, end and bottom walls, at least one pair of aligned apertures formed in selected walls of said mold cavities, a guide pin adapted for insertion through said aligned apertures, and a synthetic resinous sleeve slidably surrounding said guide pin between said selected walls through which said guide pin extends.

8. A dental articulator kit as described in claim 6, wherein a thin plate conforming to the configuration of the bottom of said mold cavity is removably disposed in said cavity and is engaged by said ejector pins when said press means is manipulated to eject said hardened dental stone "positive" from said cavity.

9. A dental articulator kit for use by a dental technician for replicating in dental stone a "positive" tooth pattern from a "negative" tooth pattern provided by a dentist, said dental articulator kit comprising:
   a) a) a support stanchion having first and second opposing end edges;
   b) a mandibular dental articulator plate having upper and lower surfaces and at least one mold cavity integrally formed on said upper surface, said mandibular dental articulator plate being mounted on one of said opposing end edges of said support stanchion;
   c) a maxillary dental articulator plate having upper and lower surfaces and at least one mold cavity integrally formed on said lower surface, said maxillary dental articulator plate being mounted on the other of said end edges of said support stanchion whereby said mold cavities on said mandibular and maxillary dental articulator plates may be selectively disposed in confronting relation; and
   d) press means including a base plate having ejector pins mounted therein and projecting therefrom, said press means selectively manipulable when one or the other of said dental articulator plates is superimposed over said ejector pins to cause said ejector pins to eject a "positive" dental stone replica cast in said one or the other of said mold cavities.

10. As an article of manufacture, a dental articulator plate, comprising:

a) a generally flat elongated base plate symmetrical in relation to a longitudinal axis and including opposed first and second surfaces;

b) at least one mold cavity integrally formed on said base plate and having integral and continuous side and end walls projecting perpendicularly from said base plate to provide free side and end edges spaced from said base plate and defining said mold cavity and within which dental stone may be deposited;

c) a plurality of apertures formed in said base plate within said at least one mold cavity and adapted to receive ejector pins that selectively penetrate said base plate and project into said cavity;

d) a removable floor plate having a peripheral edge corresponding to the inner peripheral configuration of said mold cavity and adapted to lie within said cavity to cover said plurality of apertures and prevent the passage thereinto of dental stone deposited in said cavity and adapted to be impinged by said ejector pins to eject said hardened dental stone from said cavity; and e) a mounting portion formed on one end of said base plate for mounting said articulator plate on a support structure.

11. The dental articulator plate according to claim 10, wherein said at least one mold cavity is symmetrical in relation to said longitudinal axis and includes cavity portions lying on opposite sides of said longitudinal axis.

12. The dental articulator plate according to claim 10, wherein said side walls of said cavity are provided with at least one pair of aligned apertures adapted to receive the passage of a guide pin therethrough, said pair of aligned apertures being spaced from said base plate.

13. The dental articulator plate according to claim 10, wherein said free edges of said mold cavity side walls are arcuate in configuration.

14. The dental articulator plate according to claim 10, wherein a pair of mold cavities are formed on said base plate, each mold cavity formed on opposite sides of said longitudinal axis.

15. The dental articulator plate according to claim 10, wherein randomly spaced fillets are provided within said mold cavity merging smoothly between said side walls and said base plate.

16. The dental articulator plate according to claim 10, wherein said base plate is provided with a generally ovate aperture and a generally arcuate outer peripheral edge portion and a generally arcuate inner peripheral edge portion defining a portion of the outer periphery of said generally ovate aperture.

17. The dental articulator plate according to claim 16, wherein an outer peripheral portion of said cavity side wall is coincident with an arcuate outer peripheral edge portion of said base plate, and an inner peripheral portion of said cavity side wall is coincident with an arcuate peripheral portion of said ovate aperture.

18. The dental articulator plate according to claim 10, wherein said end walls of said cavity are provided with at least one pair of aligned apertures adapted to receive the passage of a guide pin therethrough, said pair of aligned apertures being spaced from said base plate.

19. The dental articulator plate according to claim 10, wherein said side walls and said end walls of said cavity are provided with at least one pair of aligned apertures, each pair of aligned apertures in said side walls and in said end walls being adapted to receive the passage of a guide pin therethrough, said pairs of aligned apertures being spaced from said base plate.

* * * * *